US010426382B2

(12) United States Patent
Yajima et al.

(10) Patent No.: US 10,426,382 B2
(45) Date of Patent: Oct. 1, 2019

(54) DETECTION DEVICE AND DETECTION METHOD

(71) Applicant: SONY CORPORATION, Tokyo (JP)

(72) Inventors: Masakazu Yajima, Chiba (JP); Ken Hayakawa, Kanagawa (JP); Masanori Iwasaki, Kanagawa (JP); Tsukasa Yoshimura, Tokyo (JP); Naoto Yamaguchi, Tokyo (JP); Akira Tange, Tokyo (JP)

(73) Assignee: SONY CORPORATION, Tokyo (JP)

( * ) Notice: Subject to any disclaimer, the term of this patent is extended or adjusted under 35 U.S.C. 154(b) by 328 days.

(21) Appl. No.: 15/314,742

(22) PCT Filed: Jun. 5, 2015

(86) PCT No.: PCT/JP2015/066286
§ 371 (c)(1),
(2) Date: Nov. 29, 2016

(87) PCT Pub. No.: WO2015/194391
PCT Pub. Date: Dec. 23, 2015

(65) Prior Publication Data
US 2017/0196490 A1 Jul. 13, 2017

(30) Foreign Application Priority Data
Jun. 20, 2014 (JP) ................. 2014-127712

(51) Int. Cl.
*A61B 5/145* (2006.01)
*G01N 33/50* (2006.01)
(Continued)

(52) U.S. Cl.
CPC ........ *A61B 5/14507* (2013.01); *A61B 5/1455* (2013.01); *A61B 5/165* (2013.01);
(Continued)

(58) Field of Classification Search
CPC . A61B 5/14507; A61B 5/7271; A61B 5/6821; A61B 5/4824; A61B 5/1455;
(Continued)

(56) References Cited
U.S. PATENT DOCUMENTS
2001/0034500 A1* 10/2001 March ................ A61B 5/14532
604/66

FOREIGN PATENT DOCUMENTS
JP       05-093723 A     4/1993
JP       2002-528212 A   9/2002
(Continued)

OTHER PUBLICATIONS
Eye Doctors of Washington, Feb. 4, 2011, "Why Do We Cry?", https://www.edow.com/general-eye-care/crying/.*
(Continued)

*Primary Examiner* — Eric F Winakur
*Assistant Examiner* — Abid A Mustansir
(74) *Attorney, Agent, or Firm* — Chip Law Group

(57) ABSTRACT

The present technology relates to a detection device, a detection method, and a program capable of detecting a living body state of a human body easily and accurately. A contact lens type display device is provided with a tear detection unit 26 to collect tears on an eyeball and to analyze a constituent and detect affective information of a user. The detection result is sent from the contact lens type display device 11 to a mobile terminal SP and displayed on the mobile terminal SP. Consequently, the living body state can be detected on the basis of the constituent of the tears of the user, whereby the living body state of the user can be accurately detected. The present technology can be applied to a contact lens type display unit.

17 Claims, 27 Drawing Sheets

(51) Int. Cl.
*A61B 5/1455* (2006.01)
*A61B 5/16* (2006.01)
*A61B 5/00* (2006.01)
*C12Q 1/25* (2006.01)
*C12Q 1/48* (2006.01)
*G02C 7/04* (2006.01)

(52) U.S. Cl.
CPC .......... *A61B 5/4824* (2013.01); *A61B 5/6821* (2013.01); *A61B 5/7271* (2013.01); *C12Q 1/25* (2013.01); *C12Q 1/48* (2013.01); *G01N 33/50* (2013.01); *G02C 7/04* (2013.01)

(58) Field of Classification Search
CPC . A61B 5/165; G02C 7/04; C12Q 1/25; C12Q 1/48; G01N 33/50
See application file for complete search history.

(56) References Cited

FOREIGN PATENT DOCUMENTS

| | | |
|---|---|---|
| JP | 2005-502389 A | 1/2005 |
| JP | 2006-012171 A | 1/2006 |
| JP | 2010-091359 A | 4/2010 |
| JP | 2013-105319 A | 5/2013 |
| WO | 2014/052125 A1 | 4/2013 |
| WO | 2013/177465 A1 | 11/2013 |

OTHER PUBLICATIONS

Martin, et al.,"Serotonin in Human Tears", European Journal of Ophthalmology, vol. 4, No. 3, 1994, pp. 159-165.
Messmer, "Emotional tears", Der Ophthalmologe, vol. 106, Jul. 2, 2009, pp. 593-602.
Frey, et al.,"Effect of Stimulus on the Chemical Composition of Human Tears", American Journal of Ophthalmology vol. 92, No. 4, 1981, pp. 559-567.
Gelstein, et al.,"Human Tears Contain a Chesmosignal", vol. 331, www.sciencemag.org, Jan. 14, 2011, pp. 226-230.
Martin, et al.,"Serotonin in Human Tears", European Journal of Ophthalmology, vol. 4, No. 3, Jul. 1994, pp. 159-165.
Frey II, et al.,"Effect of Stimulus on the Chemical Composition of Human Tears", American Journal of Ophthalmology, vol. 92, No. 4, 1981, pp. 559-567.
Gelstein, et al.,"Human Tears Contain a Chemosignal", Science, vol. 331, www.sciencemag.org, Jan. 14, 2011, pp. 226-230.

\* cited by examiner

DETECTION DEVICE AND DETECTION METHOD

CROSS REFERENCE TO RELATED APPLICATIONS

This application is a U.S. National Phase of International Patent Application No. PCT/JP2015/066286 filed on Jun. 5, 2015, which claims priority benefit of Japanese Patent Application No. JP 2014-127712 filed in the Japan Patent Office on Jun. 20, 2014. Both of the above-referenced applications is hereby incorporated herein by reference in its entirety.

TECHNICAL FIELD

The present technology relates to a detection device, a detection method, and a program. In particular, the present technology relates to the detection device, the detection method, and the program capable of detecting a state of a living body with a high degree of accuracy.

BACKGROUND ART

In recent years, as a technology of detecting a state of a living body, for example, a technology of detecting information of an environment around a user, determining a behavior characteristic from the detected information of the environment as a living body state of the user, and reflecting a process that depends on the determined behavior characteristic in an avatar, has been proposed (refer to Patent Document 1).

CITATION LIST

Patent Document

Patent Document 1: Japanese Patent Application Laid-Open No. 2013-105319

SUMMARY OF THE INVENTION

Problems to be Solved by the Invention

However, the technology of Patent Document 1 only determines the behavior characteristic corresponding to the living body state of the user by acquiring the environmental information around the user, and reflects the process that depends on the determined behavior characteristic in the avatar. Therefore, the technology of Patent Document 1 does not directly obtain information about a living body of a person to perform the determination, whereby an appropriate process is not necessarily able to be performed.

The present technology has been made in consideration of these circumstances, particularly in order to enable a living body state of a user to be detected with a high degree of accuracy using a simplified method.

Solutions to Problems

A detection device according to an aspect of the present technology includes: an analysis unit configured to perform a constituent analysis for tears gathered from a living body; and a detection unit configured to detect a state of the living body on the basis of a result of the constituent analysis for the tears.

It is possible to cause the detection unit to detect the state of the living body that is determined in accordance with a kind of the tears on the basis of the result of the constituent analysis for the tears.

An affective state caused by an emotion of the living body can be included in the state of the living body.

It is possible to cause the detection unit to specify whether the state of the living body undergoes a transition to a predetermined affective state on the basis of an analysis result, obtained as the result of the constituent analysis for the tears, for a substance that is secreted when the state of the living body is about to undergo the transition to the predetermined affective state.

It is possible to cause the detection unit to specify whether the state of the living body undergoes a transition to either a first affective state or a second affective state on the basis of a degree of likelihood of the transition to the first affective state calculated on the basis of an analysis result, obtained as the result of the constituent analysis for the tears, for a substance that is secreted when the state of the living body is about to undergo the transition to the first affective state, and a degree of likelihood of the transition to the second affective state calculated on the basis of an analysis result, obtained as the result of the constituent analysis for the tears, for a substance that is secreted when the state of the living body is about to undergo the transition to the second affective state.

It is possible to cause the detection unit to further calculate an advance prediction emotion level indicating a degree of a state of the living body to which the state of the living body is estimated to be going to undergo a transition on the basis of the degree of the likelihood of the transition to the first affective state and the degree of the likelihood of the transition to the second affective state.

It is possible to cause the detection unit to predict a variation in the advance prediction emotion level at a time after a current time on the basis of the advance prediction emotion level.

It is possible to cause the detection unit to specify the state of the living body on the basis of an analysis result, obtained as the result of the constituent analysis for the tears, for a substance that is secreted a lot when the state of the living body is a predetermined affective state.

It is possible to cause the detection unit to specify whether the state of the tears is either a first affective state or a second affective state on the basis of a degree of likelihood of the first affective state calculated on the basis of an analysis result, obtained as the result of the constituent analysis for the tears, for a substance that is secreted a lot during the first affective state, and a degree of likelihood of the second affective state calculated on the basis of an analysis result, obtained as the result of the constituent analysis for the tears, for a substance that is secreted a lot during the second affective state.

It is possible to cause the detection unit to further calculate an emotion level indicating a degree of the affective state of the living body on the basis of the degree of the likelihood of the first affective state and the degree of the likelihood of the second affective state.

It is possible to cause the detection unit to predict a variation in the emotion level at a time after a current time on the basis of the emotion level.

A state caused by a stimulus to the living body can be included in the state of the living body.

It is possible to cause the detection unit to specify whether the state of the living body is the state caused by the stimulus to the living body or an affective state caused by an emotion of the living body to which the state of the living body undergoes a transition when the living body keeps feeling an aching pain on the basis of an analysis result, obtained as the result of the constituent analysis for the tears, for a substance that is secreted when there is the stimulus to the living body or when the living body feels the aching pain.

It is possible to cause the detection unit to specify whether the state of the living body is the state caused by the stimulus to the living body or the affective state caused by the emotion of the living body on the basis of a length of a period of time which is based on the analysis result for the substance that is secreted when there is the stimulus to the living body or when the living body feels the aching pain, and during which a value indicating a secretion amount of the substance is equal to or greater than a predetermined threshold value.

It is possible to cause the detection unit to calculate a stimulus level or an aching pain level for the living body on the basis of the analysis result for the substance that is secreted when there is the stimulus to the living body or when the living body feels the aching pain.

It is possible to cause the detection unit to predict a variation in the stimulus level or the aching pain level at a time after a current time on the basis of the stimulus level or the aching pain level.

It is possible to cause the detection unit to specify a secretion level of the tears of the living body on the basis of an analysis result, obtained as the result of the constituent analysis for the tears, for a specific substance.

The detection device can be attachable and detachable to and from an eyeball.

A detection method according to an aspect of the present technology includes the steps of: performing a constituent analysis for tears gathered from a living body; and detecting a state of the living body on the basis of a result of the constituent analysis for the tears.

A program according to an aspect of the present technology causes a computer to execute a process including: an analysis step of performing a constituent analysis for tears gathered from a living body; and a detection step of detecting a state of the living body on the basis of a result of the constituent analysis for the tears.

According to an aspect of the present technology, a constituent analysis for tears gathered from a living body is performed, and a state of the living body is detected on the basis of a result of the constituent analysis for the tears.

The detection device according to an aspect of the present technology may be an independent device, or may be a block that performs a detection process.

Effects of the Invention

According to an aspect of the present technology, a state of a living body can be detected easily and with a high degree of accuracy.

MODE FOR CARRYING OUT THE INVENTION

<Technology of Detecting State of Living Body>

The present technology detects an emotion of a person as information of a living body by detecting tears of the person that is a subject and analyzing the detected tears.

There are roughly two configuration examples of the present technology. In a first configuration example, a contact lens type display device including a function of collecting tears and analyzing the collected tears specifies a living body state of a person on the basis of information of a constituent of the analyzed tears, sends the living body state to a mobile terminal such as a smartphone, and causes the mobile terminal to display the living body state.

In addition, in a second configuration example, a contact lens type collection device executes only the collection of tears. After that, an external analysis device analyzes the collected tears, specifies a living body state of a person on the basis of information of a constituent of the analyzed tears, sends the living body state to a mobile terminal such as a smartphone, and causes the mobile terminal to display the living body state.

Figure 1:
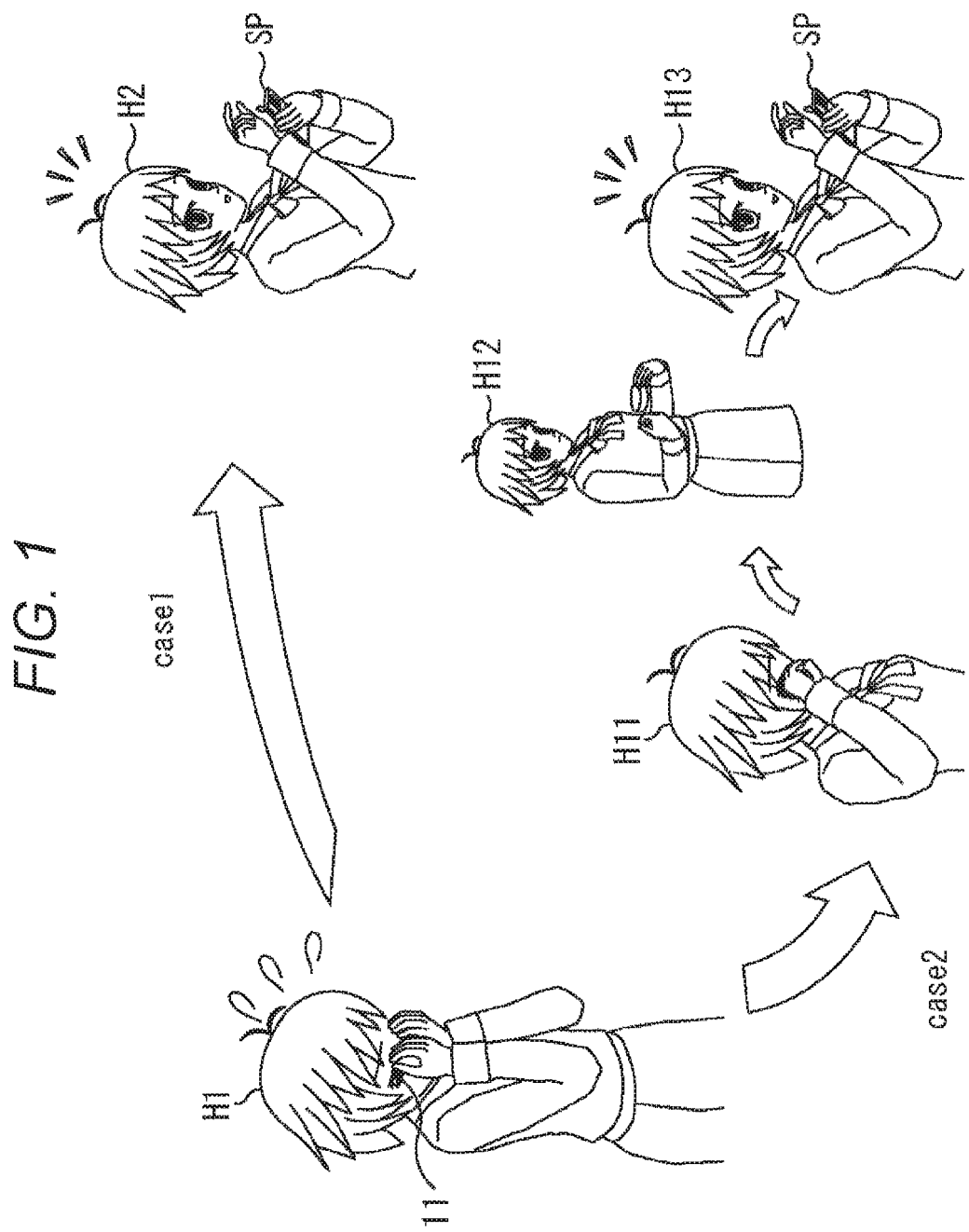
FIG. 1 is a diagram explaining a use case of a living body state detection device to which the present technology is applied.

Specifically, in the above-mentioned first configuration example, as illustrated by Case 1 in FIG. 1, a person H1 that serves as a subject wears a contact lens type display device including a function of collecting and analyzing tears. The display device then specifies a living body state on the basis of a constituent of the tears, sends the living body state to a mobile terminal SP such as a smartphone, and causes the mobile terminal SP to present the living body state. Consequently, as illustrated by a person H2 in FIG. 1, the person that serves as the subject can see information of her own living body state displayed on the mobile terminal SP.

In addition, in the above-mentioned second configuration example, as illustrated by Case 2 in FIG. 1, the person H1 that serves as a subject wears a contact lens type collection device for tears including a function of collecting tears, and once the collection of tears is competed, takes off the collection device from the eye as illustrated by a person H11. Furthermore, as illustrated by a person H12, the collection device is stored in an analysis device AN, and the analysis device AN specifies a living body state on the basis of a constituent of the tears, and sends the living body state to the mobile terminal SP such as a smartphone. Consequently, as illustrated by a person H13 in FIG. 1, the person that serves as the subject can see her own living body state displayed on the mobile terminal SP.

First Configuration Example

First, the above-mentioned first configuration example of the present technology will be described.

Figure 2:
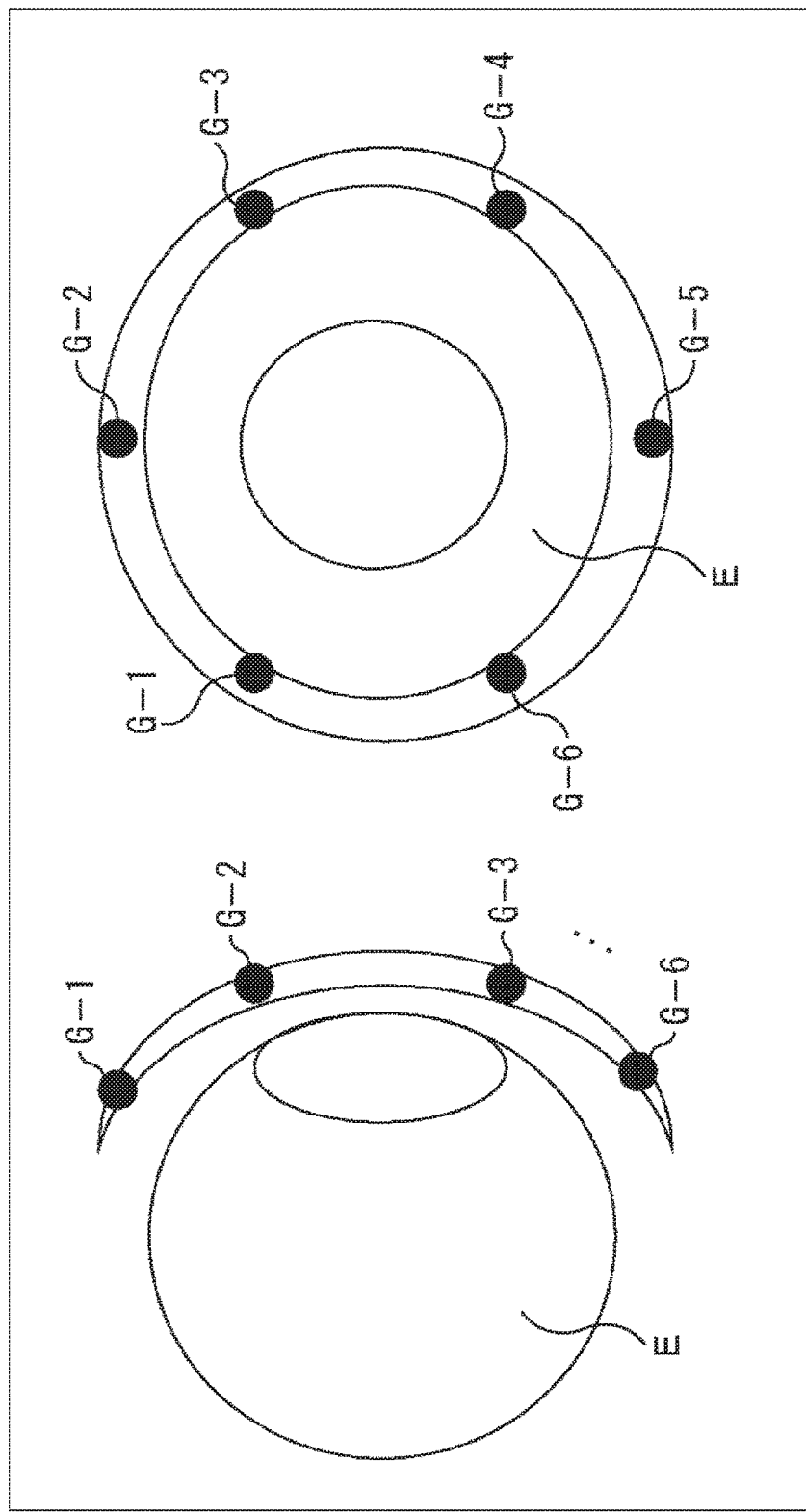
FIG. 2 is a diagram illustrating an example of wearing, on an eyeball, a contact lens type display device to which the present technology is applied.

FIG. 2 is a diagram illustrating an appearance configuration of a detection device to which the present technology is applied, namely, the contact lens type display device including the function of collecting tears and the function of analyzing the collected tears. The contact lens type display device corresponds to the above-mentioned first configuration example.

Note that a side cross section of an eyeball E on which the display device 11 is worn is illustrated in the left part of FIG. 2, and an appearance configuration of the eyeball E seen from the front is illustrated in the right part of FIG. 2. The display device 11 has a shape conforming to a curved surface of the eyeball E. As a contact lens is worn and used, so the display device 11 is worn. In addition, on an outer peripheral part of the display device 11, collection openings G-1 to G-6 for collecting tears are provided in a surface that comes into contact with the eyeball E at substantially regular intervals.

Note that although the example of providing the six collection openings G-1 to G-6 on the outer peripheral part is illustrated, a different number of collection openings may be provided. Note that when the collection openings G-1 to G-6 do not need to be distinguished from one another, they are simply referred to as a collection opening G. Other configurations are also referred to in a similar manner.

<Electrical Configuration Example of Display Device>

Figure 3:
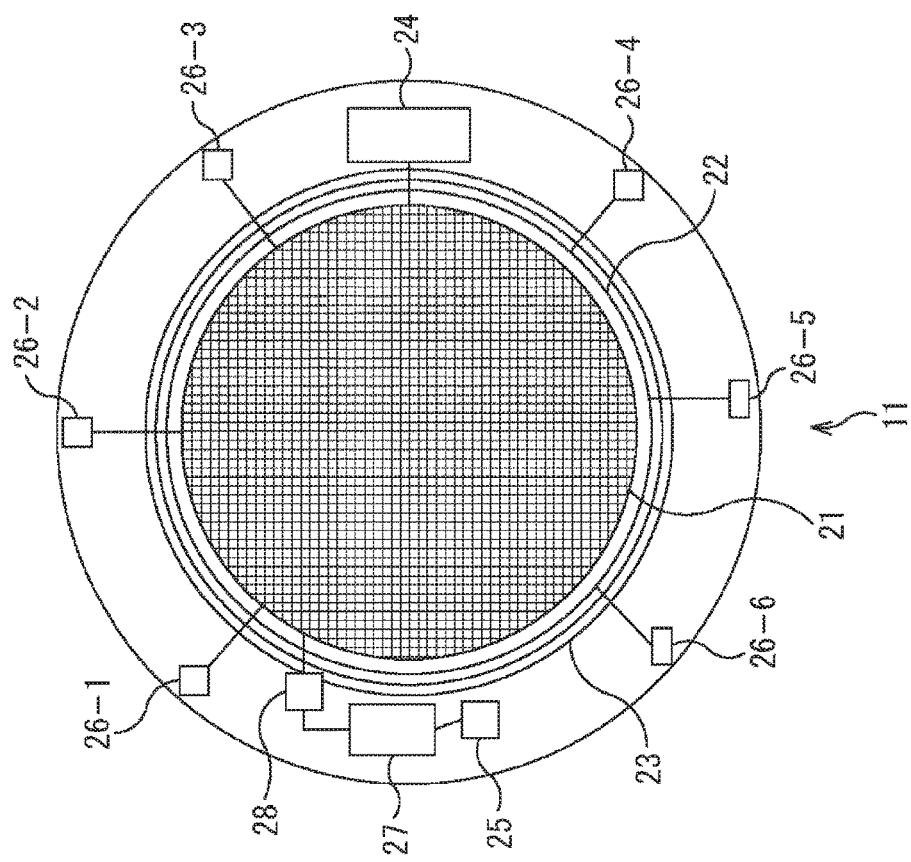
FIG. 3 is a diagram explaining an appearance configuration example of the contact lens type display device.

Next, an electrical configuration example of the display device 11 will be described with reference to FIG. 3.

Specifically, the display device 11 has a display region 21, a power supply antenna 22, a signal antenna 23, a power generation unit 24, a posture detection unit 25, a tear detection units 26-1 to 26-6, a signal processing unit 27, and a display element drive unit 28.

The display region 21 has a display element and a light receiving element for detection of a line of sight. The display element includes a plurality of display pixels that displays information such as an image and a letter to be presented to a user. The light receiving element for the detection of the line of sight is arranged adjacent to the display pixel to receive light reflected by a surface of the eyeball of the user. The display region 21 further has a light emitting element and a light receiving element for detecting opening and closing of an eyelid of the user.

The power supply antenna 22 is provided so as to surround the display region 21, and receives induced electromotive force caused by a magnetic field or an electric field and supplied from the outside. The signal antenna 23 sends, to the outside, information supplied from the signal processing unit 27 such as a result of user interface operation that is performed on the basis of the line of sight of the user. The signal antenna 23 also receives information sent from the outside such as information to be displayed on the display pixel, and supplies the information to the signal processing unit 27.

The power generation unit 24 obtains and accumulates power by rectifying an induced current generated in the power supply antenna 22 by the electromagnetic induction caused by the magnetic field or the like from the outside. The power generation unit 24 then supplies the power to each component of the display device 11. Note that the power supply antenna 22 may not be provided on the display device 11 when the power generation unit 24 itself generates power using a predetermined method or has a rechargeable battery.

The posture detection unit 25 includes an electronic gyro sensor, an acceleration sensor or the like. The posture detection unit 25 detects a posture or a motion of the user wearing the display device 11, and supplies the detection result to the signal processing unit 27. The posture detection unit 25 detects, for example, a motion of a head of the user or a posture of the user.

Each of the tear detection units 26-1 to 26-6 gathers tears secreted by the user, measures the secretion amount of the obtained tears, and performs a constituent analysis for the tears. Note that, hereinafter, when the tear detection units 26-1 to 26-6 do not particularly need to be distinguished, they are also simply referred to as a tear detection unit 26.

The signal processing unit 27 controls the entire display device 11. The signal processing unit 27 detects the line of sight of the user by detecting a dissimilarity (difference) in the light reception amount between the light receiving elements arranged in the respective regions of the display device 11 on the basis of, for example, a signal supplied from the light receiving element for the detection of the line of sight in the display region 21. The signal processing unit 27 also detects the opening and the closing of the eyelid of the user on the basis of, for example, a signal supplied from the light receiving element for the detection of the opening and the closing of the eyelid in the display region 21.

The signal processing unit 27 further controls the display element drive unit 28 on the basis of, for example, the detection result supplied from the posture detection unit 25, the result of the detection of the line of sight, and the information received by the signal antenna 23. The signal processing unit 27 then causes the display region 21 to display an image or the like.

More specifically, for example, when the display device 11 rotates with respect to the eyeball of the user, the rotation direction and the rotation amount can be detected in the posture detection unit 25. In response to this, the signal processing unit 27 controls the display element drive unit 28 to rotate the image displayed on the display region 21 by the rotation amount of the display device 11 in a direction opposite to the rotation direction of the display device 11, supplied from the posture detection unit 25, with respect to the eyeball. Consequently, even when the display device 11 rotates on the eyeball of the user, the rotation of the image that occurs as the result of the rotation of the display device 11 is corrected, and the image can be presented to the user with a high degree of visibility.

The display element drive unit 28 drives the display element in the display region 21 under the control of the signal processing unit 27 to cause the display region 21 to display the image. The display element drive unit 28 also causes the light emitting element in the display region 21 to emit light under the control of the signal processing unit 27.

<Functional Configuration Example of Display Device>

Next, a functional configuration example of the above-described display device 11 will be described.

Figure 4:
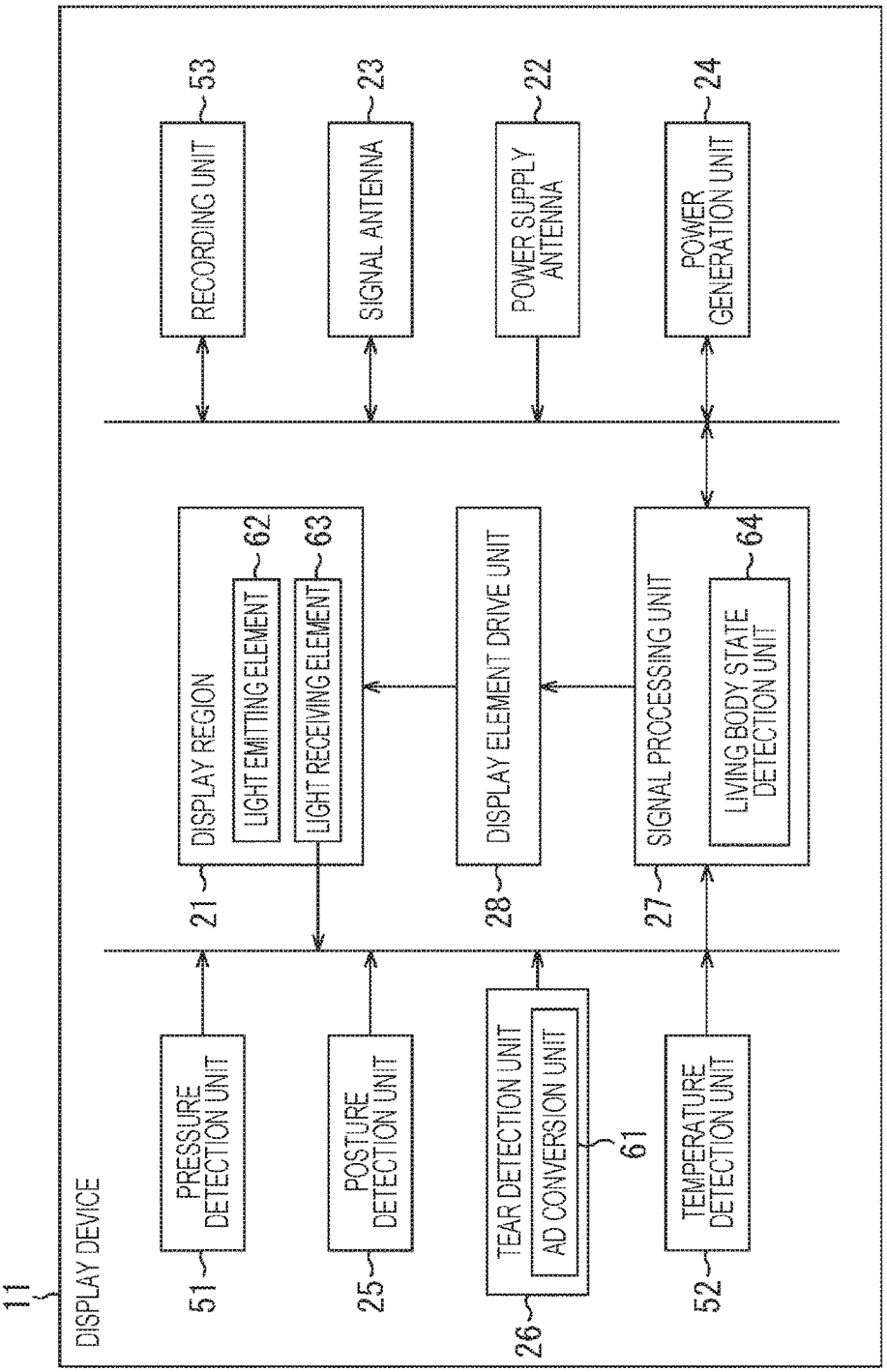
FIG. 4 is a block diagram explaining a configuration that realizes a function of the display device in FIG. 3.

The functional configuration of the display device 11 is, for example, the configuration illustrated in FIG. 4. Note that, in FIG. 4, a component corresponding to that in FIG. 2 is denoted by the same reference sign, and the description thereof is appropriately omitted.

The display device 11 illustrated in FIG. 4 has the display region 21, the power supply antenna 22, the signal antenna 23, the power generation unit 24, the posture detection unit 25, the tear detection unit 26, the signal processing unit 27, the display element drive unit 28, a pressure detection unit 51, a temperature detection unit 52, and a recording unit 53.

In addition, the light emitting element 62 and the light receiving element 63 are provided in the display region 21. Moreover, the tear detection unit 26 includes an AD conversion unit 61. Furthermore, the signal processing unit 27 has a living body state detection unit 64.

The pressure detection unit 51 includes a pressure sensor or the like. The pressure detection unit 51 detects the pressure applied to the display device 11, and outputs the detection result. The output from the pressure detection unit 51 is used, for example, for determination of the opening and the closing of the eyelid or the like.

The temperature detection unit 52 includes a plurality of temperature sensors. The temperature detection unit 52 measures the temperature of the surface of the eyeball of the user, the temperature of the eyelid of the user, or the ambient temperature, and outputs the measurement result.

The recording unit 53 includes, for example, a non-volatile memory or the like. The recording unit 53 records data supplied from the signal processing unit 27, and supplies the recorded data to the signal processing unit 27.

Moreover, in the display device 11, the output from the light receiving element 63, the pressure detection unit 51, the posture detection unit 25, the tear detection unit 26, and the temperature detection unit 52 is supplied to the signal processing unit 27. Furthermore, in the display device 11, the recording unit 53, the signal antenna 23, the power supply antenna 22, and the power generation unit 24 are also connected to the signal processing unit 27.

The analog-digital (AD) conversion unit 61 converts various types of data supplied to the tear detection unit 26 into digital signals, and supplies the digital signals to the signal processing unit 27.

The living body state detection unit 64 accepts, from the tear detection unit 26, the supply of the measurement of the secretion amount of the tears secreted by the user and the constituent analysis for the tears. The living body state detection unit 64 also detects the living body state of the user on the basis of the measurement result and the analysis result.

<Configuration Example of Tear Detection Unit>

Next, a configuration example of the tear detection unit 26 will be described with reference to FIG. 5. Each tear detection unit 26 is provided at a position corresponding to the collection opening G, detects the tears collected by the collection opening G, and further analyzes the constituent of the detected tears. Note that, in FIG. 5, the left part is a front diagram of the tear detection unit 26, and the right part in the drawing is a side diagram.

The tear detection unit 26 includes a surface including a fine hole 81 and in contact with the collection opening G, a gauge chamber 82, a channel 83, a differential pressure flowmeter 84, control valves 85-1 and 85-2, analysis chambers 86-1 to 86-5, a micropump 87, and a discharge valve 88. The tear detection unit 26 further includes the analog-digital (AD) conversion unit 61.

The fine hole 81 includes a capillary, and collects tears L using the capillary action through the collection opening G to supply the tears L to the gauge chamber 82 as illustrated in the drawing. The gauge chamber 82 includes an electrode which is not illustrated, and detects the volume of the collected tears. The detection result is supplied to the AD conversion unit 61 and output as a digital signal.

The tears accumulated in the gauge chamber 82 are conveyed to the analysis chamber 86 through the channel 83 using the micropump 87. Meanwhile, the channel 83 is provided with the differential pressure flowmeter 84, in which the flow rate of the tears conveyed through the channel 83 is measured. The measurement result is supplied to the AD conversion unit 61 and output as a digital signal.

The analysis chambers 86-1 to 86-5 respectively analyze constituents of substances a to e, supply the analysis results to the AD conversion unit 61, and cause the AD conversion unit 61 to output the analysis results as digital signals. Note that a detailed configuration of the analysis chamber 86 will be described later in detail with reference to FIG. 6. Note that the substances a to e are the names that are used for identification of the substances, and are not the actual names of the substances.

An opening degree of each of the control valves 85-1 and 85-2 is controlled by a control unit which is not illustrated in order to adjust the amount of circulating tears in accordance with the flow rate measured by the differential pressure flowmeter 84.

The discharge valve 88 is opened and closed under the control of a control unit which is not illustrated, and discharges the tears after the analysis from a discharge opening.

Figure 5:
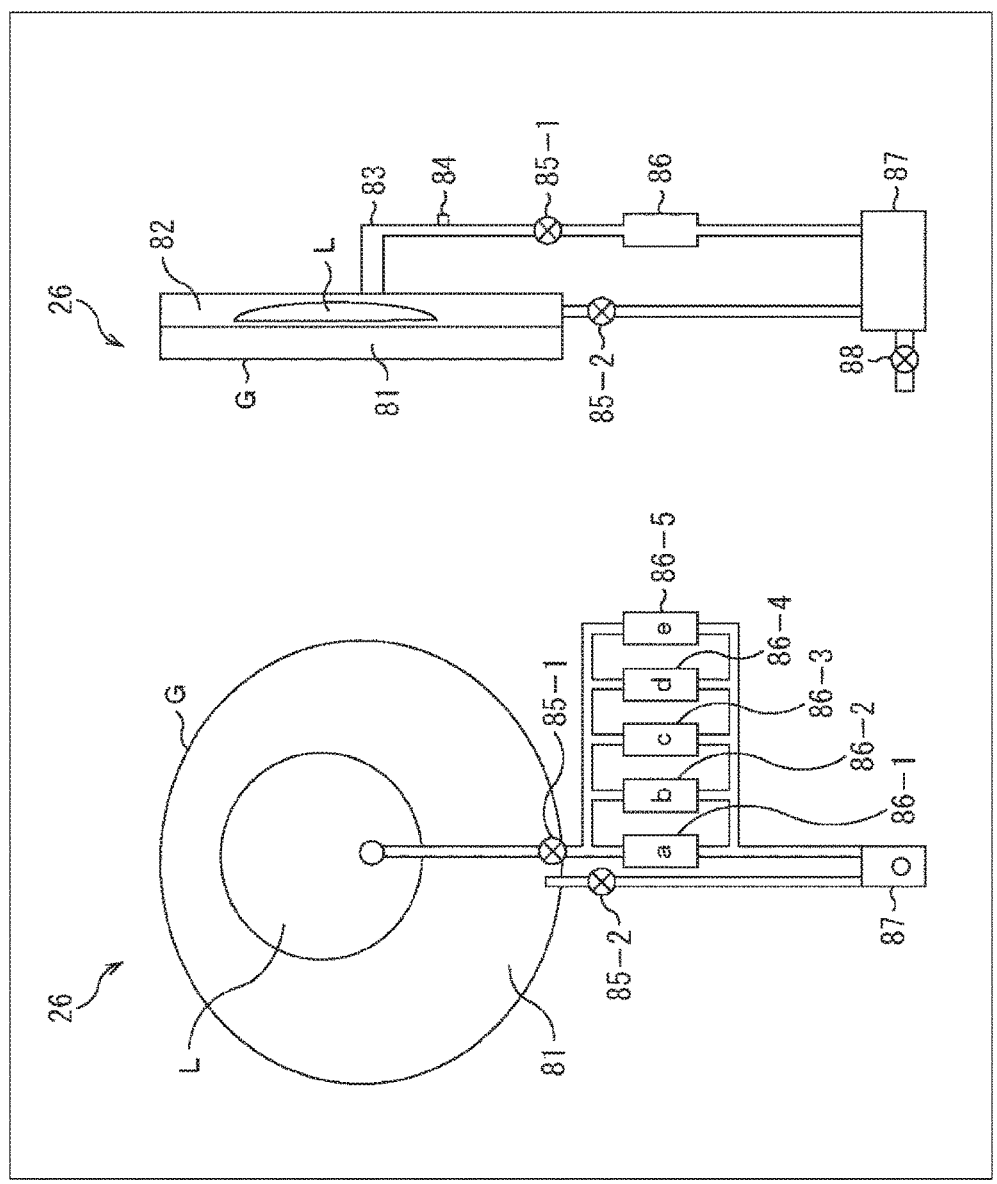
FIG. 5 is a diagram explaining a configuration example of a tear analysis unit.

Note that although the example of providing the five analysis chambers 86-1 to 86-5 is illustrated in FIG. 5, a different number of analysis chambers 86 may be provided.

<Configuration Example of Analysis Chamber>

Figure 6:
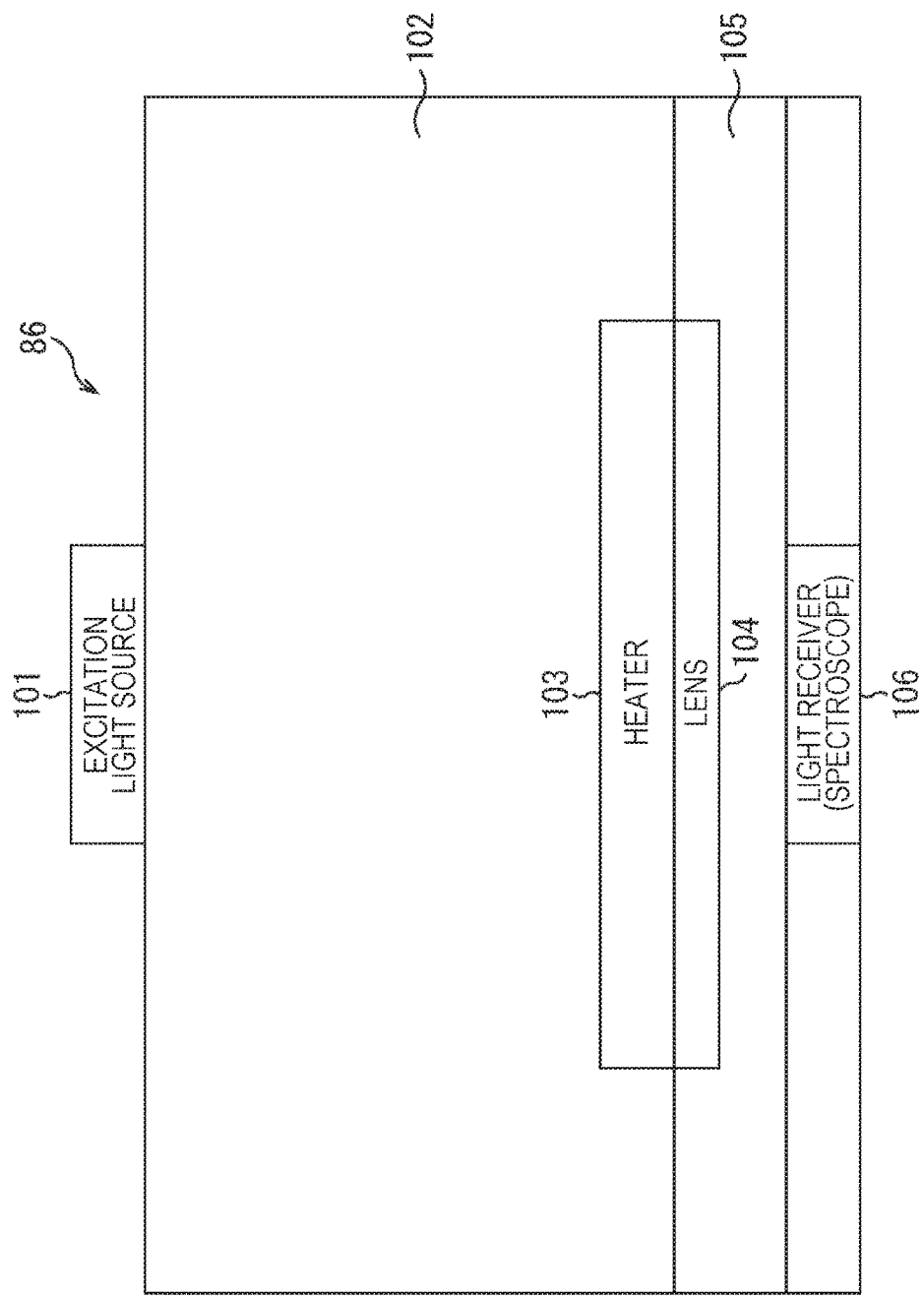
FIG. 6 is a diagram explaining a configuration example of an analysis chamber.

Next, a configuration example of the above-mentioned analysis chamber 86 will be described with reference to FIG. 6.

The analysis chamber 86 includes an excitation light source 101, an analysis space 102, a heater 103, a lens 104, and a light receiver (spectroscopic analysis unit) 106.

The excitation light source 101 generates and radiates excitation light while the substance that is a subject is evaporated (or sublimated) by the heater 103, and the analysis space 102 is filled with the vaporized substance. At this time, a spectral spectrum corresponding to the vaporized substance is generated. The lens 104 causes the light receiver (spectroscopic analysis unit) 106 to collect the spectral spectrum.

The light receiver 106 analyzes and specifies the substance that is the subject using the spectral spectrum. The light receiver 106 also supplies information of the specified detection object to the AD conversion unit 106, and causes the AD conversion unit 106 to output the information of the specified detection object as a digital signal.

An air gap 105 is an air layer for reducing the heat transfer and provided to prevent the eyeball from being injured by the heat generated in the heater 103. Specifically, the analysis chamber 86 is configured such that the lower part in the drawing comes into contact with the eyeball when the display device 11 is worn on the eyeball. Therefore, when the heating is performed by the heater 103 in this state, the generated heat is transmitted to the eyeball, and might cause a heat injury to the eyeball. Since the air gap 105 is a space filled with air having a relatively low heat transfer coefficient, the transmission of the heat generated by the heater 103 to the eyeball is reduced, and the heat injury or the like to the eyeball is prevented.

<Living Body Information Detection Process>

Figure 7:
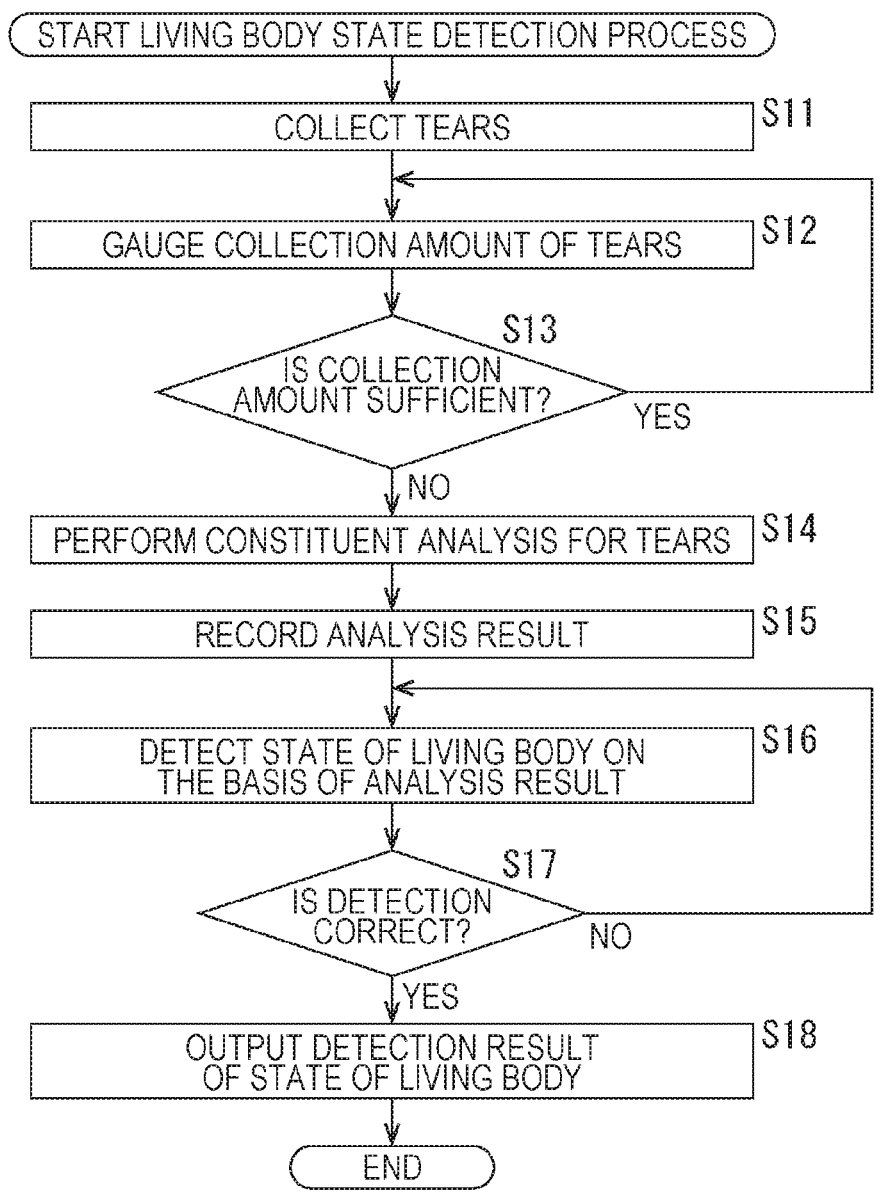
FIG. 7 is a flowchart explaining a living body state detection process.

Next, a living body information detection process will be described with reference to a flowchart in FIG. 7.

In step S11, tears on the eyeball are collected by the fine hole 81 through the collection opening G using the capillary action, and supplied to the gauge chamber 82.

In step S12, the gauge chamber 82 gauges the collection amount of the collected tears, and supplies the gauge result to the AD conversion unit 61. The AD conversion unit 61 converts the collection amount of the tears into a digital signal, and supplies the digital signal to the living body state detection unit 64 of the signal processing unit 27.

In step S13, the living body state detection unit 64 determines whether the collection amount is sufficient. Specifically, since the analysis accuracy is likely to be reduced when the collection amount of the tears is small, it is determined whether the collection amount reaches such a collection amount as to be detectable with a predetermined degree of accuracy.

When the collection amount is considered not sufficient in step S13, the process returns to step S12. In other words, the processes in steps S12 and S13 are repeated until the collection amount is considered sufficient.

After that, when the collection amount is considered sufficient in step S13, the process proceeds to step S14.

In step S14, the analysis chamber 86 analyzes the collected tears by means of the spectroscopic analysis, and outputs the analysis result to the AD conversion unit 61. The AD conversion unit 61 digitizes the analysis result, and outputs the digitized analysis result to the living body state detection unit 64 of the signal processing unit 27.

In step S15, the living body state detection unit 64 controls the recording unit 53 to cause the recording unit 53 to record the analysis result.

In step S16, the biological state detection unit 64 detects the state of the living body on the basis of the analysis result.

In step S17, the biological state detection unit 64 determines whether the living body state is correct and appropriate. Specifically, when the state of the living body that is based on the analysis result is a result which should not be true in principle, the process returns to step S16. In this case, a similar result is obtained unless, for example, the analysis method is changed. Therefore, for example, a threshold value or the like is changed, and the processes in steps S16 and S17 are repeated. Note that as to whether the state of the living body is a result which should be true in principle, information required for the determination such as a threshold value may be set in advance, or the user may directly perform the determination, and information that depends on the determination may be input. At this time, the method of determining the state of the living body that depends on the analysis result may be changed by the user.

After that, when it is determined that the detected state of the living body is correct and appropriate in step S17, the process proceeds to step S18.

In step S19, the living body state detection unit 64 controls the signal antenna 23 to send the detected living body information to the mobile terminal SP represented by a smartphone or the like, and cause the mobile terminal SP to display the detected living body information.

Owing to the above-mentioned processes, the state of the living body is displayed on the mobile terminal SP. Therefore, the user can recognize the living body state without being particularly conscious of it. Meanwhile, it can also be considered that the analysis method is learned when the processes in steps S16 and S17 are repeated while the analysis method or the threshold value is changed until the appropriate state of the living body is considered to be detected in step S17.

Therefore, in a case where the learning is completed, and whether the living body information is appropriate no longer needs to be determined in step S17, the process in step S17 may be omitted.

Figure 8:
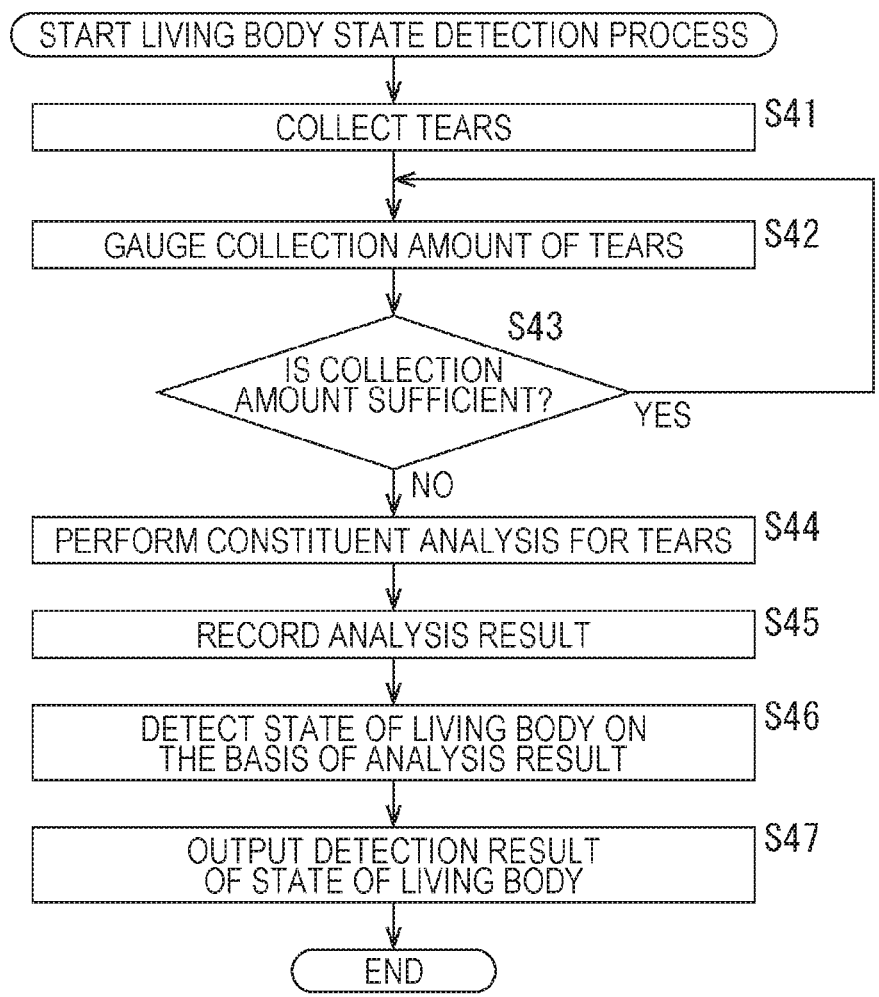
FIG. 8 is a flowchart explaining another living body state detection process.

FIG. 8 is a flowchart explaining the living body state detection process from which the process of determining whether the living body information is appropriate corresponding to step S17 is omitted. In other words, processes in steps S41 to S47 in the flowchart of FIG. 8 correspond to the processes in steps S11 to S16 and S17 in FIG. 7. Note that since the respective processes are similar to the processes described with reference to the flowchart of FIG. 7, the description of the living body state detection process in FIG. 8 is omitted.

<Relation between State of Tears and Living Body State>

Figure 9:
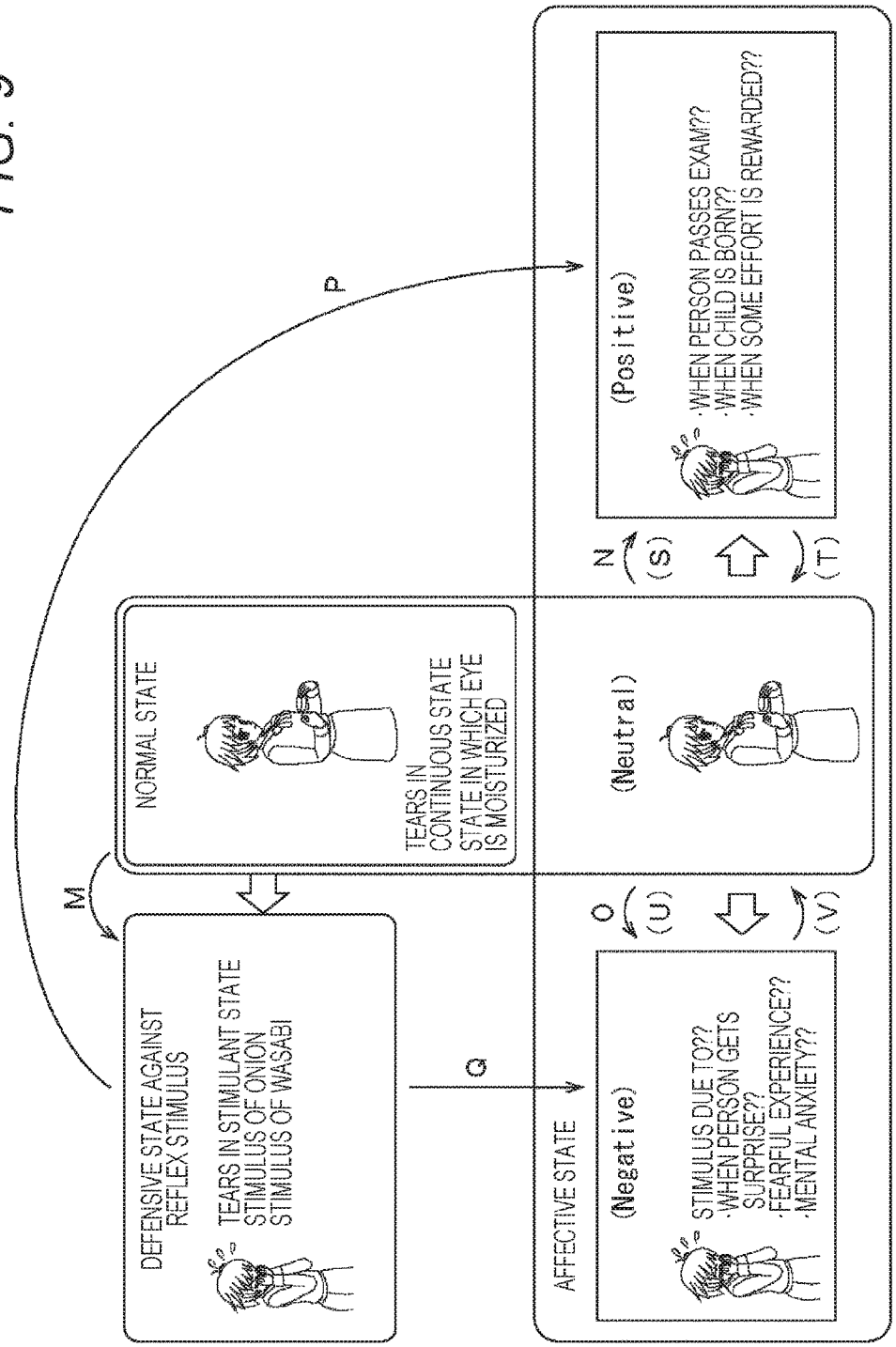
FIG. 9 is a diagram explaining a transition of a living body state.

Next, a relation between a state of tears and the living body state will be described using an example with reference to FIG. 9. Note that any of the states in FIG. 9 is a living body state. In addition, any of M, N, O, P, Q, R, S, and T is a constituent of tears that contributes to a state transition of the living body state in an arrow direction, and they are hereinafter referred to as constituents M, N, O, P, Q, R, S, and T, respectively.

The living body state that depends on the state of the tears is roughly classified into three states, that is, divided into a normal state, a defensive state against a reflex stimulus, and an affective state.

As used herein, the normal state represents a state in which a film of tears is formed over the eyeball with a blink in order to protect the eye. The tears in this state are referred to as continuous tears. Therefore, in a case where the state of the tears is the continuous tears, the living body state is defined as the normal state.

In addition, the defensive state against the reflex stimulus represents a state in which more tears are shed than those in the state of shedding the continuous tears due to a foreign substance put into the eye or a stimulus such as allyl sulfide of an onion in order to protect the eye. Such tears are referred to as tears in a stimulant state. Hereinafter, this state is also referred to as the defensive state.

Furthermore, the affective state is a state in which tears are shed with emotional effusion such as during a joyful occasion and a sorrowful occasion. Such tears are also referred to as emotion tears.

The tears in the affective state are further classified into three kinds, i.e., tears in an affective (positive) state, tears in an affective (neutral) state, and tears in an affective (negative) state.

The tears in the affective (positive) state represent tears in a state in which the emotion is changed to the positive state such as when, for example, the person passes an exam, a child is born, some effort is rewarded, and the negative state is changed to the positive state at once.

The tears in the affective (neutral) state represent, for example, tears in a state in which the affective (positive) state and the affective (negative) state are balanced. In this regard, the tears in the state in which the affective (positive) state and the affective (negative) state are balanced are tears in a continuous state. However, since a typical human is in a state of a transition to either of them in accordance with an individual difference, the affective (neutral) state is defined as an initial state of the tears in the affective state for convenience.

The tears in the affective (negative) state represent tears in a state in which the emotion is changed to the negative state such as when, for example, the person gets a surprise, has a fearful experience, and suffers mental anxiety. Note that tears that are shed when the person hits her little toe on something and keeps feeling an aching pain for quite a while, and the emotion becomes the negative state, are classified as the tears in the affective (negative) state.

Note that since any of the above-mentioned normal state and affective (neutral) state (initial state) has the tears in the continuous state, the description will be provided on the assumption that the normal state is also included in the initial state.

The constituent M is a constituent of tears that contributes to a transition from the initial state to the defensive state. The constituent M is, for example, lactoferrin, substance P or the like. When the constituent M increases in a short time and reaches a threshold value, it can be determined that the state undergoes the transition to the defensive state. In other words, owing to the change in the constituent M, it is possible to grasp whether a pain is perceived by the user or cannot be perceived by the user.

The constituent N is a constituent of tears that contributes to a transition from the initial state to the affective (positive) state. The constituent N is, for example, adrenaline or the like. When the constituent N increases and reaches a threshold value, it can be determined that the state is the affective (positive) state. In other words, owing to the change in the constituent N, it is possible to grasp whether exaltation or excitement of feelings is perceived by the person herself or cannot be perceived by the person herself.

The constituent O is a constituent of tears that contributes to a transition from the initial state to the affective (negative) state. The constituent O is, for example, adrenocorticotropic hormone (ACTH), noradrenaline or the like. When the constituent O reaches a threshold value, it can be determined that the state is the affective (negative) state. In other words, owing to the change in the constituent O, it is possible to grasp whether stress or frustration is perceived by the person herself or cannot be perceived by the person herself.

The constituent Q is a constituent that contributes to a transition from the defensive state to the affective state. The constituent Q is, for example, lactoferrin, substance P or the like. When the constituent Q is kept at a threshold value for a long time, it can be determined that the state is the affective state (deriving from an aching pain). Note that although the constituent Q is used for the determination of a state similar to that in the constituent M, the constituent Q is characterized by the long duration time of the threshold value. Owing to the change in the constituent Q, it is possible to grasp whether a continuing pain is perceived by the person herself or cannot be perceived by the person herself.

The constituent P is a constituent that contributes to a transition from the defensive state to the affective (positive) state. The constituent Q is a constituent that contributes to a transition from the defensive state to the affective (negative) state.

In addition, the above-mentioned constituent N as well as the constituent P serves as the constituent that contributes to the transition to the affective (positive) state, and the constituent O as well as the constituent Q serves as the constituent that contributes to the transition to the affective (negative) state. Therefore, in accordance with a ratio obtained when each of the constituents N, O, P, and Q reaches the threshold value, a mutual state and level between the affective (positive) state and the affective (negative) state can be grasped.

Therefore, in a case where only an affective absolute value, that is, only whether the state is the affective (positive) state or the affective (negative) state, is to be grasped, when an increase or decrease in a constituent deriving from both the constituent N or the constituent P and the constituent O or the constituent Q reaches a threshold value, it can be determined that the state is the related affective state.

The constituent S is a constituent that indicates an omen of a subsequent transition from the initial state to the affective (positive) state. The constituent S is, for example, phenylethanolamine N-methyltransferase or the like. When the constituent S reaches a threshold value, it can be determined that the omen of the subsequent transition to the affective (positive) state occurs.

The constituent T is a constituent that indicates an omen of a subsequent transition from the affective (positive) state to the initial state.

A constituent U is a constituent that indicates an omen of a subsequent transition from the initial state to the affective (negative) state. When the constituent U, e.g., hydrocortisone (cortisol) or the like, reaches a threshold value, it can be determined that the omen of the subsequent transition to the affective (negative) state occurs.

A constituent V is a constituent that indicates an omen of a subsequent transition from the affective (negative) state to the initial state. When the constituent V, e.g., corticotropin-releasing hormone or the like, reaches a threshold value, it can be determined that the omen of the subsequent transition to the initial state occurs.

Specifically, the constituent T or the constituent V is the constituent that indicates an omen of a subsequent suppression of an affective absolute value. Therefore, when a constituent deriving from both the constituent T or the constituent V, i.e., serotonin, monoamine oxidase, catechol-O-methyltransferase or the like, reaches a threshold value, it can be determined that the omen of the subsequent transition to the initial state occurs.

<Relation Between Constituent of Tears and Time Transition>

Figure 10:
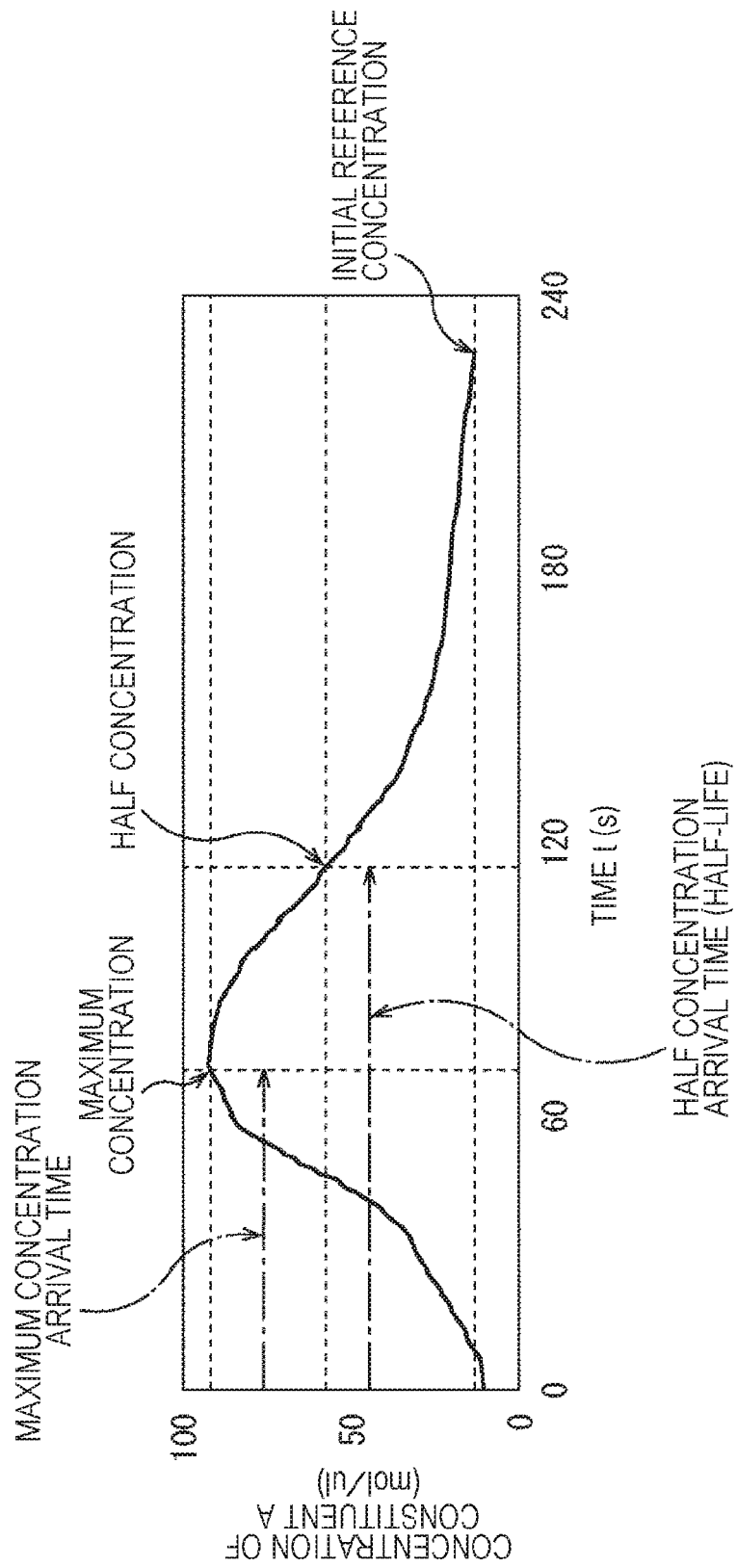
FIG. 10 is a diagram explaining a relation between a constituent of tears and a time transition.

Next, a relation between a constituent of tears and a time transition will be described with reference to FIG. 10. In FIG. 10, a vertical axis indicates a concentration of a constituent A, and a horizontal axis indicates elapsed time t(s). Note that the change on the second (s) time scale is illustrated in FIG. 10.

As illustrated in FIG. 10, it is illustrated that a period of time from an initial reference concentration to a maximum concentration is a maximum concentration arrival time. It is also illustrated that a period of time from the initial reference concentration through the maximum concentration to a half concentration is a half concentration arrival time.

Figure 11:
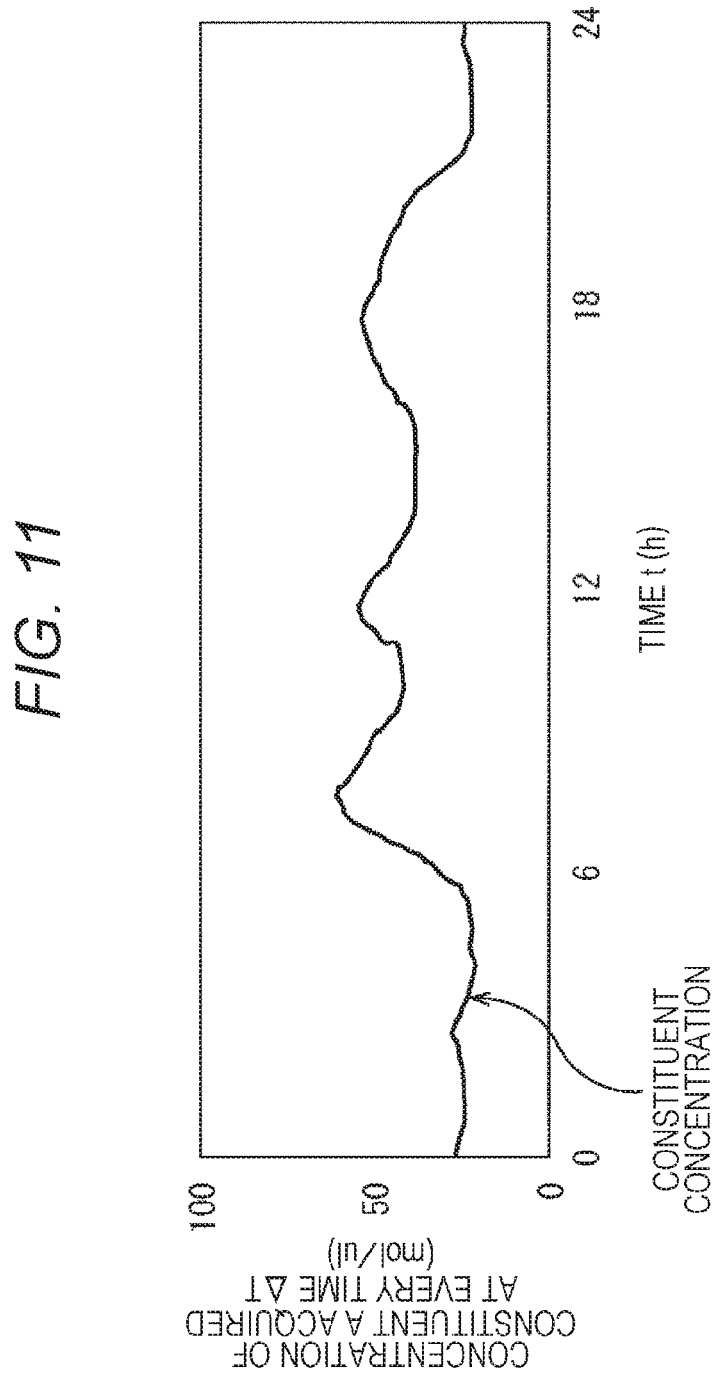
FIG. 11 is a diagram explaining a relation between a cumulated constituent of tears and a time transition.

As illustrated in FIG. 10, some constituents of tears vary with a lapse of about several hundred seconds. As illustrated in FIG. 11, others change due to a lapse of about several hours. Note that a variation in the cumulative constituent A at every predetermined time $\Delta t$ is illustrated in FIG. 11. A vertical axis is a cumulative value (integrated value) of the concentration of the constituent A per $\Delta t$, and a horizontal axis is elapsed time T(s). In FIG. 11, a unit of time is an hour.

Therefore, with regard to the change in the constituent of the tears, the change needs to be determined using, for example, the variation amount (slope of the graph) or a variation pattern that is adapted to appropriate elapse of time in accordance with the substance or the like. For example, the elapse of time is changed on the second time scale, the minute time scale, the hour time scale, or the day time scale.

<Emotion Advance Prediction Computation Process>

Figure 12:
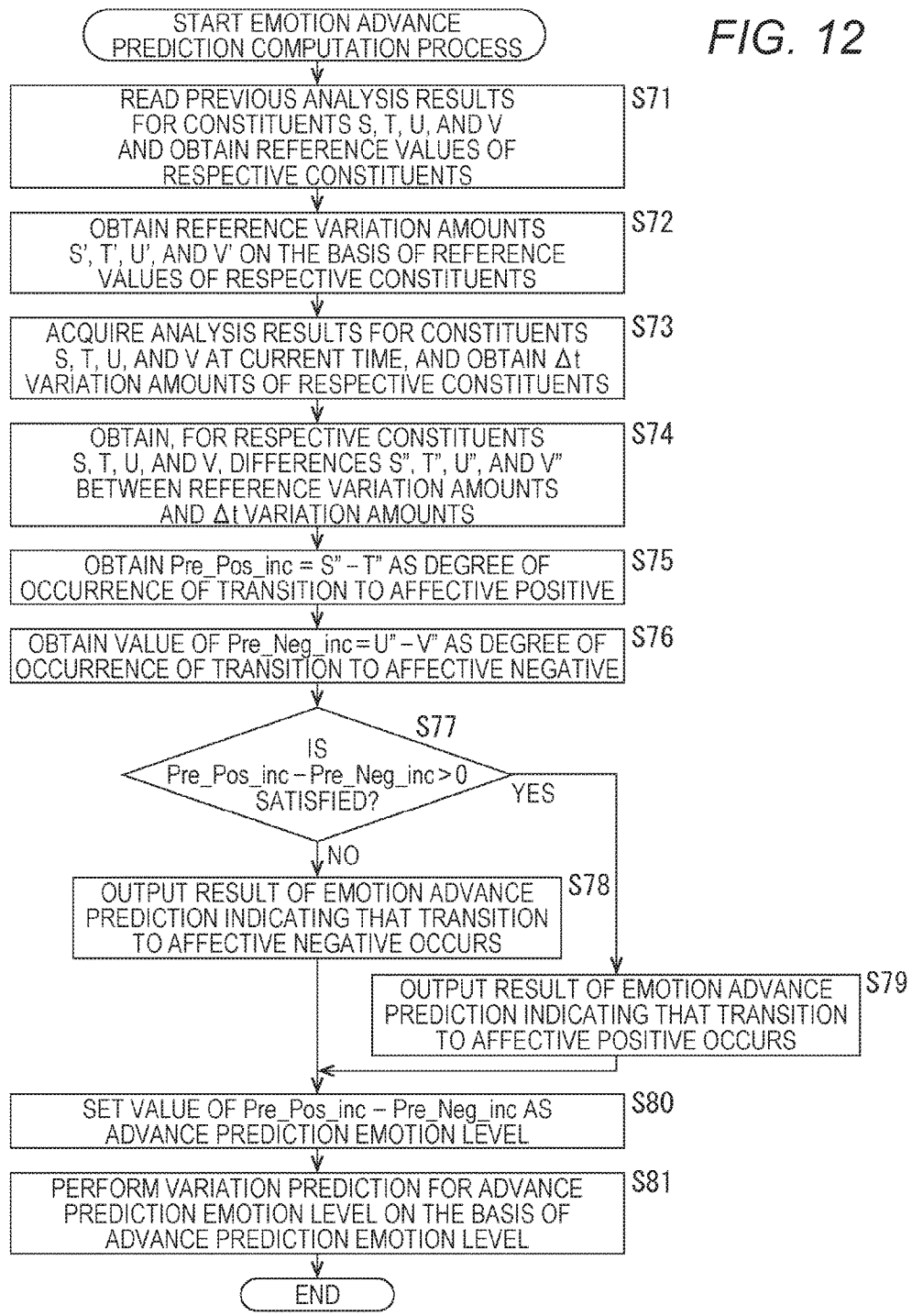
FIG. 12 is a flowchart explaining an emotion advance prediction computation process.

Next, an emotion advance prediction computation process will be described with reference to a flowchart in FIG. 12.

In step S71, the living body state detection unit 64 reads previous analysis results for the constituents S, T, U, and V from the recording unit 53, and obtains reference values of the respective constituents. Specifically, since the previously obtained analysis results for the constituents S, T, U, and V are recorded in the recording unit 53, they are read.

In step S72, the living body state detection unit 64 obtains reference variation amounts S', T', U', and V' on the basis of the reference values of the respective constituents.

In step S73, the living body state detection unit 64 reads analysis results for the constituents S, T, U, and V at a current time from the recording unit 53, and obtains variation amounts $S\Delta t$, $T\Delta t$, $U\Delta t$, and $V\Delta t$ that are $\Delta t$ variation amounts of the respective constituents.

In step S74, the living body state detection unit 64 obtains, for the constituents S, T, U, and V, differences S", T", U", and V" ($=\alpha 1$ ($S\Delta t-S'$), $\alpha 2$ ($T\Delta t-T'$), $\alpha 3$ ($U\Delta t-U'$), and $\alpha 4$ ($V\Delta t-V'$)) between the $\Delta t$ variation amounts, namely, the variation amounts $S\Delta t$, $T\Delta t$, $U\Delta t$, and $V\Delta t$, and the reference variation amounts S', T', U', and V'. Note that $\alpha 1$ to $\alpha 4$ are constituent coefficients. In other words, a secretion ratio of each constituent is converted into the coefficient for normalizing a numerical value to be compared.

In step S75, the living body state detection unit 64 calculates a degree Pre_Pos_inc of occurrence of the transition to the affectivity (positive) (affective positive) as a difference (S"−T").

In step S76, the living body state detection unit 64 calculates a degree Pre_Neg_inc of occurrence of the transition to the affectivity (negative) (affective negative) as a difference (U"−V").

In step S77, the living body state detection unit 64 calculates a difference (U"−V") between the degree Pre_Pos_inc of the occurrence of the transition to the affectivity (positive) and the degree Pre_Neg_inc of the occurrence of the transition to the affectivity (negative). The living body state detection unit 64 then determines whether the difference is greater than zero. In other words, the living body state detection unit 64 determines whether the transition to the affective (positive) state is likely to occur or the transition to the affectivity (negative) is likely to occur.

In step S77, when it is determined that the difference between the degree Pre_Pos_inc of the occurrence of the transition to the affectivity (positive) and the degree Pre_Neg_inc of the occurrence of the transition to the affectivity (negative) is greater than zero, and the transition to the affectivity (positive) is likely to occur, the process proceeds to step S78.

In step S79, the living body state detection unit 64 controls the display element drive unit 28, sends, to the mobile terminal SP via the signal antenna 23, information indicating that the transition to the affective (positive) state occurs, and causes the mobile terminal SP to display the information.

On the other hand, in step S77, when it is determined that the difference between the degree Pre_Pos_inc of the occurrence of the transition to the affectivity (positive) and the degree Pre_Neg_inc of the occurrence of the transition to the affectivity (negative) is less than zero, and the transition to the affectivity (negative) is likely to occur, the process proceeds to step S78.

In step S78, the living body state detection unit 64 controls the display element drive unit 28, sends, to the mobile terminal SP via the signal antenna 23, information indicating that the transition to the affective (negative) state occurs, and causes the mobile terminal SP to display the information.

In step S80, the living body state detection unit 64 sets, as an advance prediction emotion level, the difference (U"−V") between the degree Pre_Pos_inc of the occurrence of the transition to the affectivity (positive) and the degree Pre_Neg_inc of the occurrence of the transition to the affectivity (negative). The living body state detection unit 64 then records the advance prediction emotion level in the recording unit 53.

In step S81, the living body state detection unit 64 performs a variation prediction for the advance prediction emotion level on the basis of the advance prediction emotion level. The living body state detection unit 64 then controls the display element drive unit 28, sends the result of the variation prediction to the mobile terminal SP via the signal antenna 23, and causes the mobile terminal SP to display the result of the variation prediction.

Specifically, for example, when the advance prediction emotion level exceeds a predetermined threshold value, or when a predetermined period of time $\Delta T$ elapses from a timing of exceeding the threshold value, the living body state detection unit 64 causes the mobile terminal SP to display whether the transition to either the affective (positive) state or the affective (negative) state might occur. In addition, when the constituent for the affectivity (positive) increases by A, and the constituent for the affectivity (negative) decreases by B, it may be displayed whether the transition to either the affective (positive) state or the affective (negative) state might occur after the predetermined period of time $\Delta T$ elapses from the timing of exceeding the threshold value. Furthermore, a state of an emotion that is predicted from a relation between an emotion specified by an emotion computation process which will be described later and the prediction may be learned, and the prediction may be performed on the basis of the result of the learning.

Moreover, in step S71, the previously obtained analysis results for the constituents S, T, U, and V to be read are, for example, analysis results, for a predetermined period of time after the transition of the state, having the same transition pattern of the transition from a state immediately before a current state to the current state. Specifically, for example, in a case where the current state is the initial state, and the state immediately before the current state is the defensive state, previous analysis results for the constituents S, T, U, and V for the predetermined period of time after a timing of the transition from the initial state to the defensive state are read. Then, the living body state detection unit 64 obtains waveforms of the reference values from averages or the like of the previously obtained and read analysis results for the constituents S, T, U, and V. The living body state detection unit 64 calculates, as the reference variation amounts S', T', U', and V', slopes on the waveforms of the reference values at a timing that coincides with elapse of time after the transition to the current state.

In this manner, the reference variation amounts S', T', U', and V' are obtained from the previous analysis results for the constituents S, T, U, and V in the state transition pattern having the same state transition, whereby the accuracy of the emotion advance prediction computation is improved.

As a result, the transition of the affective state can be predicted in advance as the information of the living body state.

In addition, as described with reference to FIGS. 10 and 11, a setting range for the $\Delta t$ variation amount to be used is also changed on the second time scale, the minute time scale, the hour time scale, or the day time scale. Consequently, a short-term prediction or a long-term prediction is enabled. Furthermore, although the example of using the $\Delta t$ variation amount has been described so far, the advance prediction may be performed using a variation pattern in place of the $\Delta t$ variation amount.

<Emotion Computation Process>

Figure 13:
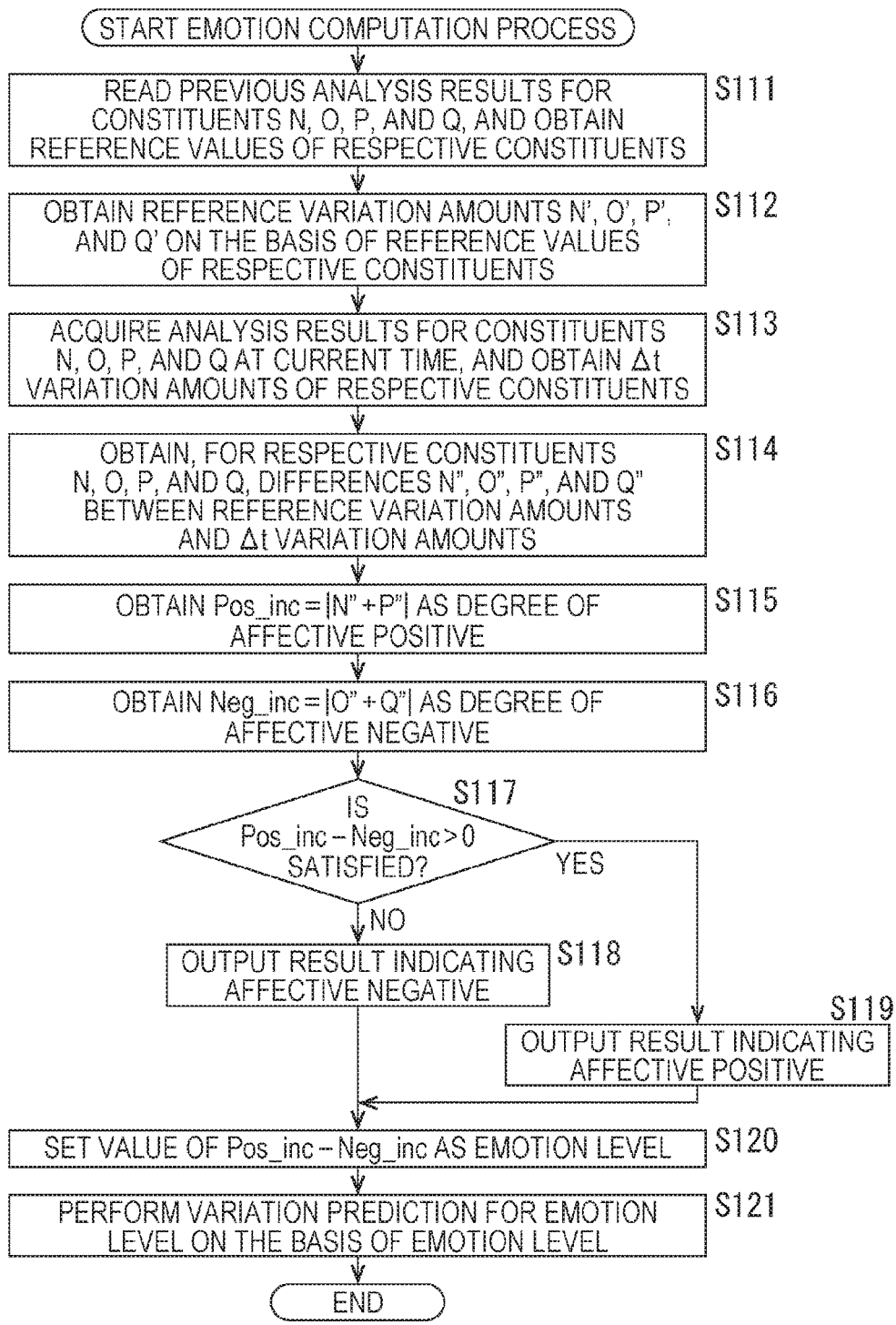
FIG. 13 is a flowchart explaining an emotion computation process.

Next, the emotion computation process will be described with reference to a flowchart in FIG. 13.

In step S111, the living body state detection unit 64 reads previous analysis results for the constituents N, O, P, and Q from the recording unit 53, and obtains reference values of the respective constituents. Specifically, since the previously obtained analysis results for the constituents N, O, P, and Q are recorded in the recording unit 53, they are read. With regard to the previously obtained analysis results for the constituents N, O, P, and Q to be read, analysis results similar in content to the analysis results for the constituents S, T, U, and V that are read in the above-mentioned step S71 are read.

In step S112, the living body state detection unit 64 obtains reference variation amounts N', O', P', and Q' on the basis of the reference values of the respective constituents.

In step S113, the living body state detection unit 64 reads analysis results for the constituents N, O, P, and Q at a current time from the recording unit 53, and obtains variation amounts N$\Delta$t, O$\Delta$t, P$\Delta$t, and Q$\Delta$t that are $\Delta t$ variation amounts of the respective constituents.

In step S114, the living body state detection unit 64 obtains, for the constituents N, O, P, and Q, differences N", O", P", and Q" (=$\beta1$ (N$\Delta$t−N'), $\beta2$ (O$\Delta$t−O'), $\beta3$ (P$\Delta$t−P'), and $\beta4$ (Q$\Delta$t−Q')) between the $\Delta t$ variation amounts, namely, the variation amounts N$\Delta$t, O$\Delta$t, P$\Delta$t, and Q$\Delta$t, and the reference variation amounts N', O', P', and Q'. Note that $\beta1$ to $\beta4$ are constituent coefficients. In other words, a secretion ratio of each constituent is converted into the coefficient for normalizing a numerical value to be compared.

In step S115, the living body state detection unit 64 calculates a degree Pos_inc of the affectivity (positive) as a sum |N"+P"|.

In step S116, the living body state detection unit 64 calculates a degree Neg_inc of the affectivity (negative) as a sum |O"+Q"|.

In step S117, the living body state detection unit 64 computes a difference between the degree Pos_inc of the affectivity (positive) and the degree Neg_inc of the affectivity (negative). The living body state detection unit 64 then determines whether the difference is greater than zero. In other words, the living body state detection unit 64 determines whether the state is the affective (positive) state.

In step S117, when it is determined that the difference between the degree Pos_inc of the affectivity (positive) and the degree Neg_inc of the affectivity (negative) is greater than zero, and the state is the affective (positive) state, the process proceeds to step S119.

In step S119, the living body state detection unit 64 controls the display element drive unit 28, sends, to the mobile terminal SP, information indicating that the state is the affective (positive) state by controlling the signal antenna 23, and causes the mobile terminal SP to display the information.

On the other hand, in step S117, when it is determined that the difference between the degree Pos_inc of the affectivity (positive) and the degree Neg_inc of the affectivity (negative) is less than zero, and the state is the affective (negative) state, the process proceeds to step S118.

In step S118, the living body state detection unit 64 controls the display element drive unit 28, sends, to the mobile terminal SP, information indicating that the state is the affective (negative) state by controlling the signal antenna 23, and causes the mobile terminal SP to display the information.

In step S120, the living body state detection unit 64 sets, as an emotion level, the difference between the degree Pos_inc of the affectivity (positive) and the degree Neg_inc of the affectivity (negative). The living body state detection unit 64 then records the emotion level in the recording unit 53.

In step S121, the living body state detection unit 64 performs a variation prediction for the emotion level on the basis of the emotion level. The living body state detection unit 64 then controls the signal antenna 23 to send the result of the variation prediction to the mobile terminal SP, and causes the mobile terminal SP to display the result of the variation prediction.

Specifically, for example, when the emotion level exceeds a predetermined threshold value, or when the predetermined period of time $\Delta T$ elapses from a timing of exceeding the threshold value, the living body state detection unit 64 causes the mobile terminal SP to display whether the transition to either the affective (positive) state or the affective (negative) state might occur. In addition, when the constituent for the affectivity (positive) increases by A, and the constituent for the affectivity (negative) decreases by B, the living body state detection unit 64 may cause the mobile terminal SP to display whether the transition to either the affective (positive) state or the affective (negative) state might occur after the predetermined period of time $\Delta T$ elapses from the timing of exceeding the threshold value.

Moreover, after the predetermined period of time elapses, the prediction may be able to be performed using data of the variation amounts of the respective constituents to which the state is input by the user, or the prediction may be performed in accordance with a correlation between the variation amounts of the respective constituents. Furthermore, environmental information such as at the time of wake-up/at the time of eating a meal/commuting/during work/going back home/conversation with a family/before bedtime, is used as external text mining data, and the prediction may be performed on the basis of a correlation with these items of external text mining data. Furthermore, the prediction after the elapse of the predetermined period of time may be performed by means of a moving average prediction or an approximate value prediction.

<Severe Pain/Aching Pain Computation Process>

Figure 14:
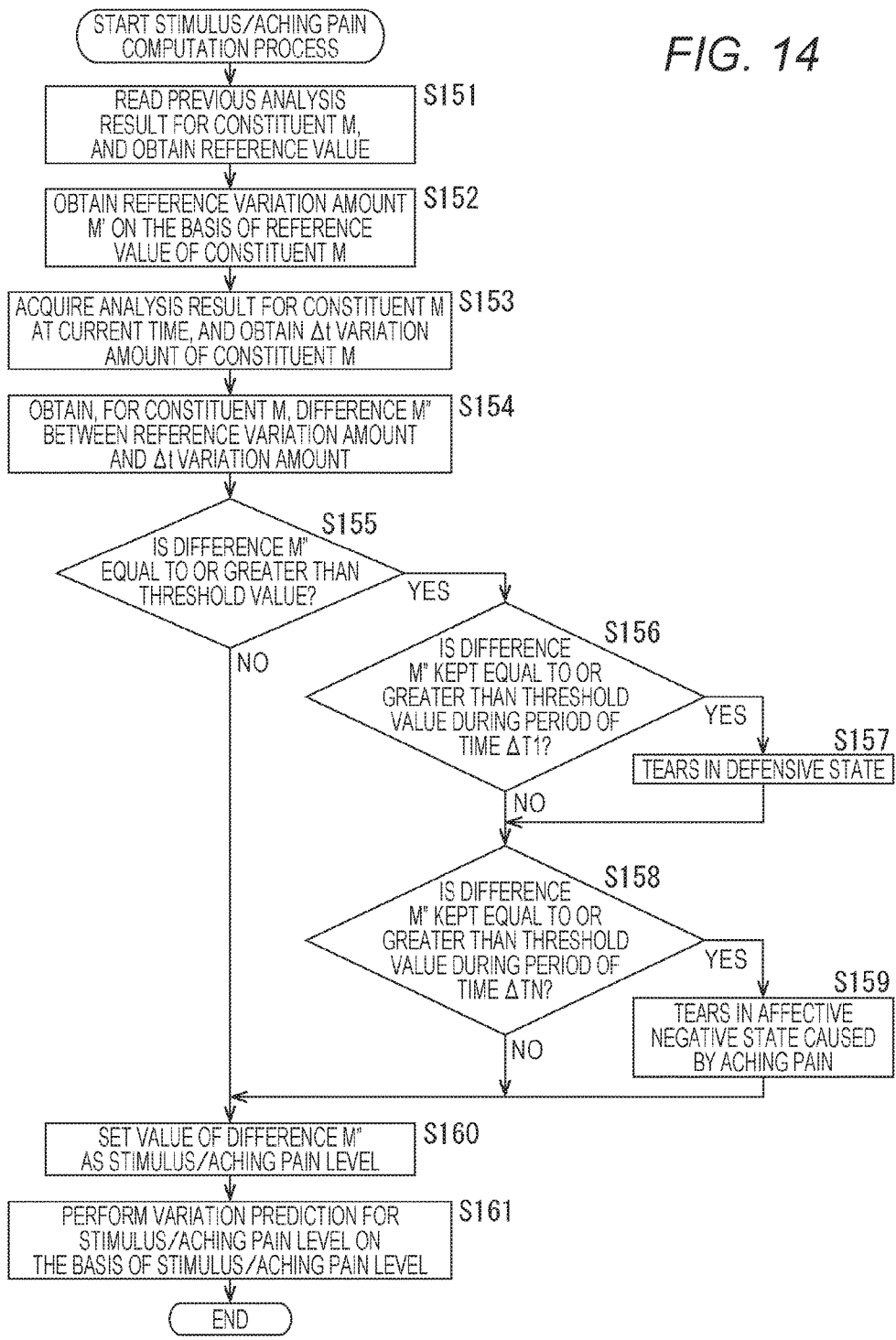
FIG. 14 is a flowchart explaining a stimulus/aching pain computation process.
Figure 15:
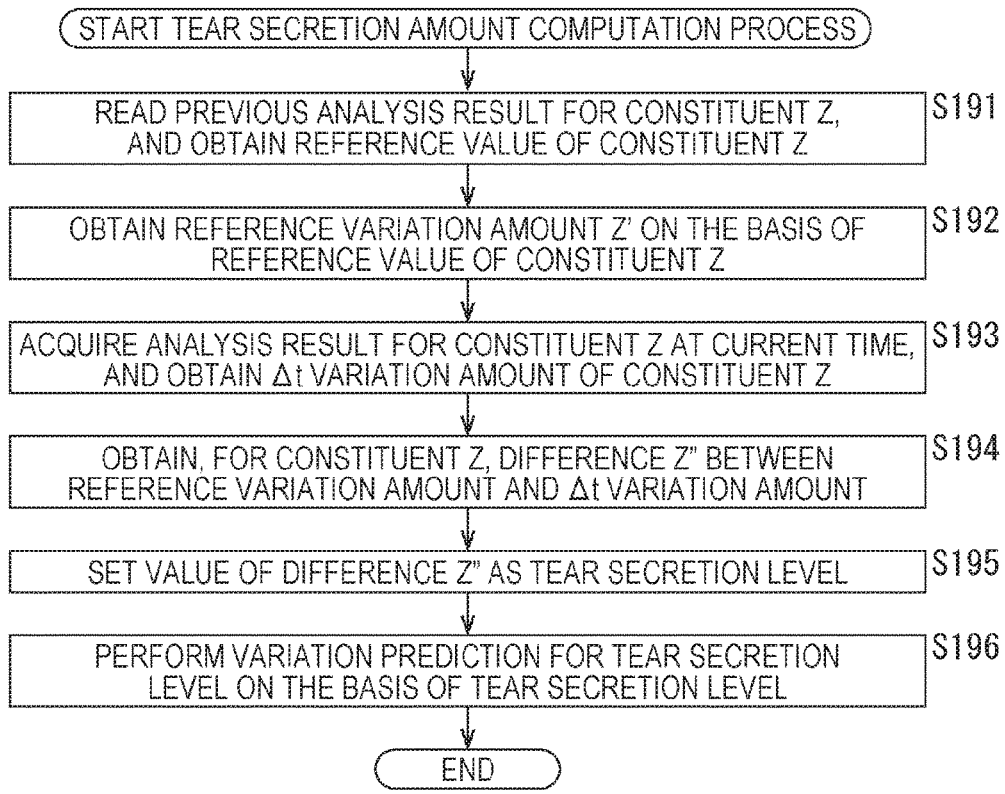
FIG. 15 is a flowchart explaining a tear secretion amount computation process.

Next, a severe pain/aching pain computation process will be described with reference to a flowchart in FIG. 14.

In step S151, the living body state detection unit 64 reads a previous analysis result for the constituent M from the recording unit 53, and obtains a reference value of the constituent. Specifically, since the previously obtained analysis result for the constituent M is recorded in the recording unit 53, it is read.

In step S152, the living body state detection unit 64 obtains a reference variation amount M' on the basis of the reference value of the constituent M.

In step S153, the living body state detection unit 64 reads an analysis result for the constituent M at a current time from the recording unit 53, and obtains a variation amount M$\Delta$t that is a $\Delta$t variation amount of the constituent M.

In step S154, the living body state detection unit 64 obtains, for the constituent M, a difference M" (=$\gamma$1 (M$\Delta$t−M') between the $\Delta$t variation amount, namely, the variation amount M$\Delta$t, and the reference variation amount M'. Note that $\gamma$1 is a constituent coefficient. In other words, a secretion ratio of each constituent is converted into the coefficient for normalizing a numerical value to be compared.

In step S155, the living body state detection unit 64 determines whether the difference M" is greater than a predetermined threshold value. In other words, the living body state detection unit 64 determines whether the state is the affectivity (negative) caused by an aching pain or the defensive state.

In step S155, when it is determined that the difference M" is greater than the threshold value, the state is considered the affectivity (negative) caused by the aching pain or the defensive state, and the process proceeds to step S156.

In step S156, the living body state detection unit 64 determines whether the difference M" is kept greater than the threshold value during a period of time $\Delta$T1, i.e., about five to six minutes.

In step S156, when the difference M" is considered to be kept greater than the threshold value during the period of time $\Delta$T1, i.e., about five to six minutes, the process proceeds to step S157.

In step S157, the living body state detection unit 64 controls the display element drive unit 28, sends, to the mobile terminal SP, information indicating that the state is the defensive state by controlling the signal antenna 23, and causes the mobile terminal SP to display the information. Specifically, when the constituent M is greater than the threshold value for a somewhat short time, the possibility of the external stimulus is high. Therefore, it is determined that the state is the defensive state.

On the other hand, in step S156, when the difference M" is considered not to be kept greater than the threshold value during the period of time $\Delta$T1, i.e., about five to six minutes, the process in step S157 is skipped.

In step S158, the living body state detection unit 64 determines whether the difference M" is kept greater than the threshold value during a period of time $\Delta$TN, i.e., about a day.

In step S158, when the difference M" is considered to be kept greater than the threshold value during the period of time $\Delta$TN, i.e., about a day, the process proceeds to step S159.

In step S159, the living body state detection unit 64 controls the display element drive unit 28, sends, to the mobile terminal SP, information indicating that the state is the affective (negative) state caused by the aching pain by controlling the signal antenna 23, and causes the mobile terminal SP to display the information. Specifically, when the constituent M is greater than the threshold value for a somewhat long period of time, i.e., about a day, the pain continues even though it is originally caused by the external stimulus. Therefore, it is determined that the state is the affective (negative) state caused by the aching pain.

On the other hand, in step S158, when the difference M" is considered not to be kept greater than the threshold value during the period of time $\Delta$TN, i.e., about a day, the process in step S159 is skipped.

In step S160, the living body state detection unit 64 sets the difference M" as a stimulus/aching pain level, and records the stimulus/aching pain level in the recording unit 53.

In step S161, the living body state detection unit 64 performs a variation prediction for the stimulus/aching pain level on the basis of the stimulus/aching pain level. The living body state detection unit 64 then controls the display element drive unit 28, sends the result of the variation prediction to the mobile terminal SP by controlling the signal antenna 23, and causes the mobile terminal SP to display the result of the variation prediction.

Specifically, for example, the living body state detection unit 64 may predict how a change in a new stimulus/aching pain level undergoes a transition in accordance with a trend analysis of a variation pattern of the stimulus/aching pain level, and cause the mobile terminal SP to display the prediction.

In addition, the living body state detection unit 64 may predict how the change in the stimulus/aching pain level undergoes a transition when the stimulus/aching pain level exceeds a threshold value, or when a predetermined period of time elapses after the stimulus/aching pain level exceeds the threshold value.

Furthermore, after the predetermined period of time elapses, the living body state detection unit 64 may predict the change in the stimulus/aching pain level using data of the variation amounts of the respective constituents to which the state is input by the user. Moreover, the living body state detection unit 64 may predict the change in the stimulus/aching pain level in accordance with a correlation with the variation amount of each constituent.

Furthermore, the living body state detection unit 64 may store the environmental information such as at the time of wake-up/at the time of eating a meal/commuting/during work/going back home/conversation with a family/before bedtime, together with the external text mining data to perform the prediction. Alternatively, the living body state detection unit 64 may perform the prediction after the elapse of the predetermined period of time by means of the moving average prediction or the approximate value prediction.

In addition, the living body state detection unit 64 not only predicts whether the variation in the stimulus/aching pain level that cannot be recognized by the user occurs, and notifies the user, but also may inform a medical institution or the like as necessary in accordance with the stimulus/aching pain level.

<Tear Secretion Amount Computation Process>

So far, the process of specifying the state of the living body by detecting the constituent that contributes to the transition from the state of the living body of the user such as the affective state and the defensive state against the reflex stimulus described with reference to FIG. 9 to another state, and the process of predicting how the state of the living body subsequently changes have been described. Therefore, these processes can also be applied to a living body state which is not defined in FIG. 9 by detecting a constituent that contributes to a transition to a predetermined living body state.

For example, manganese(II) chloride or manganese(III) oxide that induces secretion of tears may be measured as a constituent Z, and applied to a tear secretion amount computation process for computing the tear secretion amount. Therefore, next, the tear secretion amount computation process will be described with reference to a flowchart in FIG. 14.

In step S191, the living body state detection unit 64 reads a previous analysis result for the constituent Z from the recording unit 53, and obtains a reference value of the constituent. Specifically, since the previously obtained analysis result for the constituent Z is recorded in the recording unit 53, it is read.

In step S192, the living body state detection unit 64 obtains a reference variation amount Z' on the basis of the reference value of the constituent Z.

In step S193, the living body state detection unit 64 reads an analysis result for the constituent Z at a current time from the recording unit 53, and obtains a variation amount $Z\Delta t$ that is a $\Delta t$ variation amount of the constituent Z.

In step S194, the living body state detection unit 64 obtains, for the constituent Z, a difference Z" ($=\Theta 1$ ($Z\Delta t-Z'$)) between the $\Delta t$ variation amount, namely, the variation amount $Z\Delta t$, and the reference variation amount Z'. Note that $\Theta 1$ is a constituent coefficient. In other words, a secretion ratio of each constituent is converted into the coefficient for normalizing a numerical value to be compared.

In step S195, the living body state detection unit 64 sets the difference Z" as a tear secretion level, and records the tear secretion level in the recording unit 53.

In step S196, the living body state detection unit 64 performs a variation prediction for the tear secretion level on the basis of the tear secretion level. The living body state detection unit 64 then controls the display element drive unit 28, sends the result of the variation prediction to the mobile terminal SP by controlling the signal antenna 23, and causes the mobile terminal SP to display the result of the variation prediction.

Specifically, for example, the living body state detection unit 64 may predict how a change in a new tear secretion level undergoes a transition in accordance with a trend analysis of a variation pattern of the tear secretion level, and cause the mobile terminal SP to display the prediction.

In addition, the living body state detection unit 64 may predict how the change in the tear secretion level undergoes a transition when the tear secretion level exceeds a threshold value, or when a predetermined period of time elapses after the tear secretion level exceeds the threshold value.

Furthermore, after the predetermined period of time elapses, the living body state detection unit 64 may predict the change in the tear secretion level using data of the variation amounts of the respective constituents to which the state is input by the user. Moreover, the living body state detection unit 64 may predict the change in the tear secretion level in accordance with a correlation with the variation amount of the constituent O or the constituent Q (adrenocorticotropic hormone (ACTH)).

Furthermore, the living body state detection unit 64 may store the environmental information such as at the time of wake-up/at the time of eating a meal/commuting/during work/going back home/conversation with a family/before bedtime, together with the external text mining data to perform the prediction. Alternatively, the living body state detection unit 64 may perform the prediction after the elapse of the predetermined period of time by means of the moving average prediction or the approximate value prediction.

<Awakening/Dormancy Advance Prediction Computation Process>

So far, the example of predicting the tear secretion amount by means of the constituent Z has been described. Then, for example, using the constituents S, T, U, and V, a living body state may be detected in an awakening/dormancy advance prediction in such a manner that, using a method similar to that for the example of executing the advance emotion prediction computation process, an advance awakening constituent and an advance dormancy constituent are defined, and an awakening/dormancy advance prediction computation process is executed. As used herein, the advance awakening constituent is, for example, adrenaline or the like, and the advance dormancy constituent is noradrenaline or the like.

Figure 16:
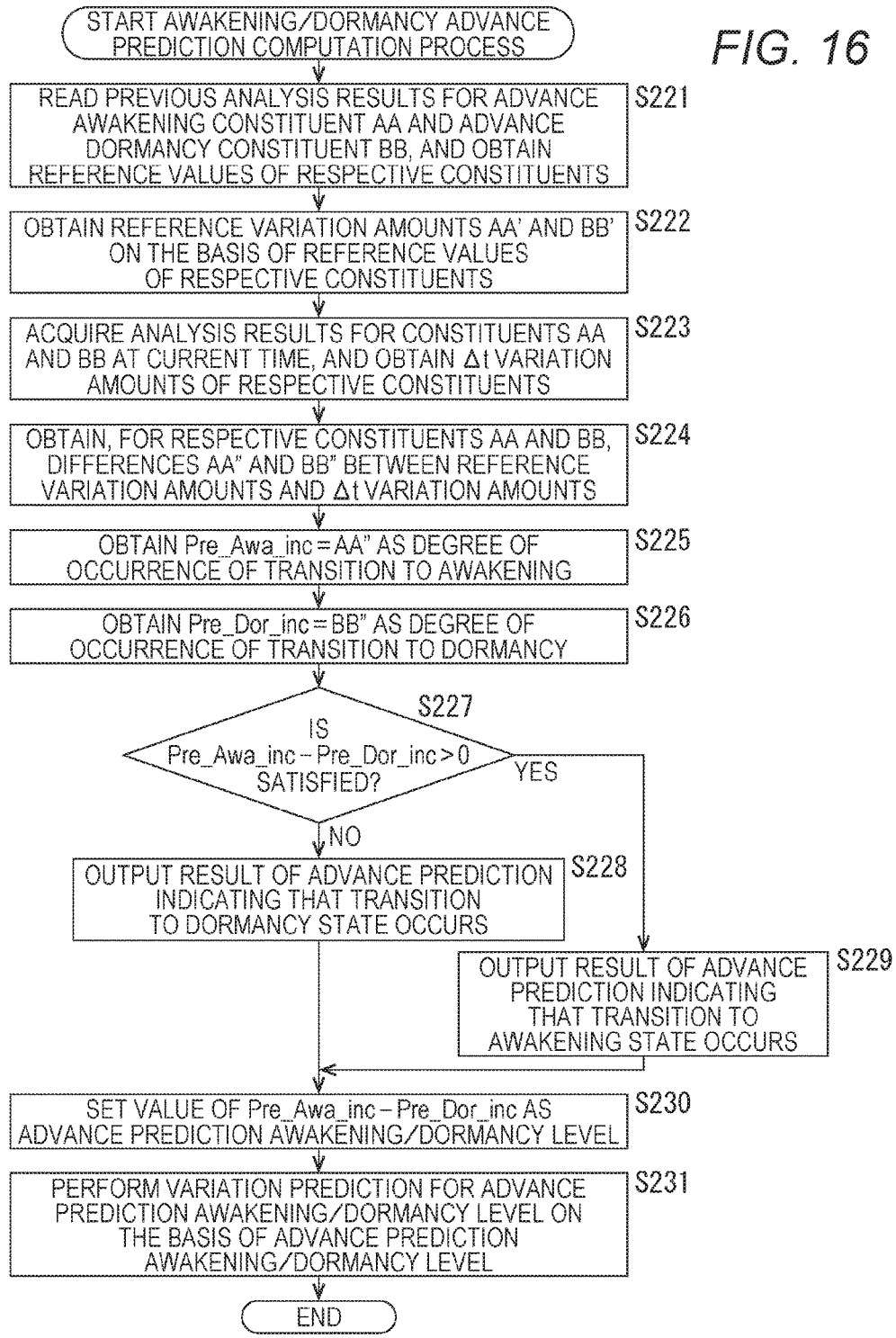
FIG. 16 is a flowchart explaining an awakening/dormancy computation process.

Therefore, next, the awakening/dormancy advance prediction computation process will be described with reference to a flowchart in FIG. 16.

In step S221, the living body state detection unit 64 reads previous analysis results for the advance awakening constituent AA and the advance dormancy constituent BB from the recording unit 53, and obtains reference values of the respective constituents. Specifically, since the previously obtained analysis results for the constituents AA and BB are recorded in the recording unit 53, they are read.

In step S222, the living body state detection unit 64 obtains reference variation amounts AA' and BB' on the basis of the reference values of the respective constituents.

In step S223, the living body state detection unit 64 reads analysis results for the constituents AA and BB at a current time from the recording unit 53, and obtains variation amounts $AA\Delta t$ and $BB\Delta t$ that are $\Delta t$ variation amounts of the respective constituents.

In step S224, the living body state detection unit 64 obtains, for the constituents AA and BB, differences AA" and BB" ($=\eta 1$ ($AA\Delta t-AA'$) and $\eta 2$ ($BB\Delta t-BB'$)) between the $\Delta t$ variation amounts, namely, the variation amounts $AA\Delta t$ and $BB\Delta t$, and the reference variation amounts AA' and BB'. Note that $\eta 1$ and $\eta 2$ are constituent coefficients. In other words, a secretion ratio of each constituent is converted into the coefficient for normalizing a numerical value to be compared.

In step S225, the living body state detection unit 64 calculates a degree Pre_Awa_inc of occurrence of the transition to the awakening as AA".

In step S226, the living body state detection unit 64 calculates a degree Pre_Dor_inc of occurrence of the transition to the dormancy as BB".

In step S227, the living body state detection unit 64 calculates a difference between the degree Pre_Awa_inc of the occurrence of the transition to the awakening and the degree Pre_Dor_inc of the occurrence of the transition to the dormancy. The living body state detection unit 64 then determines whether the difference is greater than zero. In other words, the living body state detection unit 64 determines whether the transition to the awakening is likely to occur or the transition to the dormancy is likely to occur.

In step S227, when it is determined that the difference between the degree Pre_Awa_inc of the occurrence of the transition to the awakening and the degree Pre_Dor_inc of the occurrence of the transition to the dormancy is greater than zero, and the transition to the awakening is likely to occur, the process proceeds to step S229.

In step S229, the living body state detection unit 64 controls the signal antenna 23 to send, to the mobile terminal SP, information indicating that the transition to the awakening state occurs, and causes the mobile terminal SP to display the information.

On the other hand, in step S227, when it is determined that the difference between the degree Pre_Awa_inc of the occurrence of the transition to the awakening and the degree Pre_Dor_inc of the occurrence of the transition to the dormancy is less than zero, and the transition to the dormancy is likely to occur, the process proceeds to step S228.

In step S228, the living body state detection unit 64 controls the signal antenna 23 to send, to the mobile terminal SP, information indicating that the transition to the dormancy state occurs, and causes the mobile terminal SP to display the information.

In step S230, the living body state detection unit 64 sets, as an advance prediction awakening/dormancy level, the difference between the degree Pre_Awa_inc of the occurrence of the transition to the awakening and the degree Pre_Dor_inc of the occurrence of the transition to the dormancy. The living body state detection unit 64 then records the difference in the recording unit 53.

In step S231, the living body state detection unit 64 performs a variation prediction for the advance prediction awakening/dormancy level on the basis of the advance prediction awakening/dormancy level. The living body state detection unit 64 then controls the signal antenna 23 to send the result of the variation prediction to the mobile terminal SP, and causes the mobile terminal SP to display the result of the variation prediction.

Specifically, for example, when the advance prediction awakening/dormancy level exceeds a predetermined threshold value, or when the predetermined period of time $\Delta T$ elapses from a timing of exceeding the threshold value, the living body state detection unit 64 causes the mobile terminal SP to display whether the transition to either the awakening state or the dormancy state might occur. In addition, when the constituent for the awakening increases by A, and the constituent for the dormancy decreases by B, the living body state detection unit 64 may cause the mobile terminal SP to display whether the transition to either the awakening state or the dormancy state might occur after the predetermined period of time $\Delta T$ elapses from the timing of exceeding the threshold value. Furthermore, a state of an emotion that is predicted from a relation between an emotion specified by an awakening/dormancy computation process which will be described later and the prediction may be learned, and the prediction may be performed on the basis of the result of the learning.

After the predetermined period of time elapses, the living body state detection unit 64 may perform the prediction using data of the variation amounts of the respective constituents to which the state is input by the user. In addition, the living body state detection unit 64 may predict the advance prediction awakening/dormancy level in accordance with a correlation with the variation amount of the constituent O or the constituent Q (adrenocorticotropic hormone (ACTH)). The living body state detection unit 64 may also predict the environmental information such as at the time of wake-up/at the time of eating a meal/commuting/during work/going back home/conversation with a family/before bedtime, together with the external text mining data. Furthermore, the living body state detection unit 64 may perform the prediction after the elapse of the predetermined period of time by means of the moving average prediction or the approximate value prediction.

<Awakening/Dormancy Computation Process>

Figure 17:
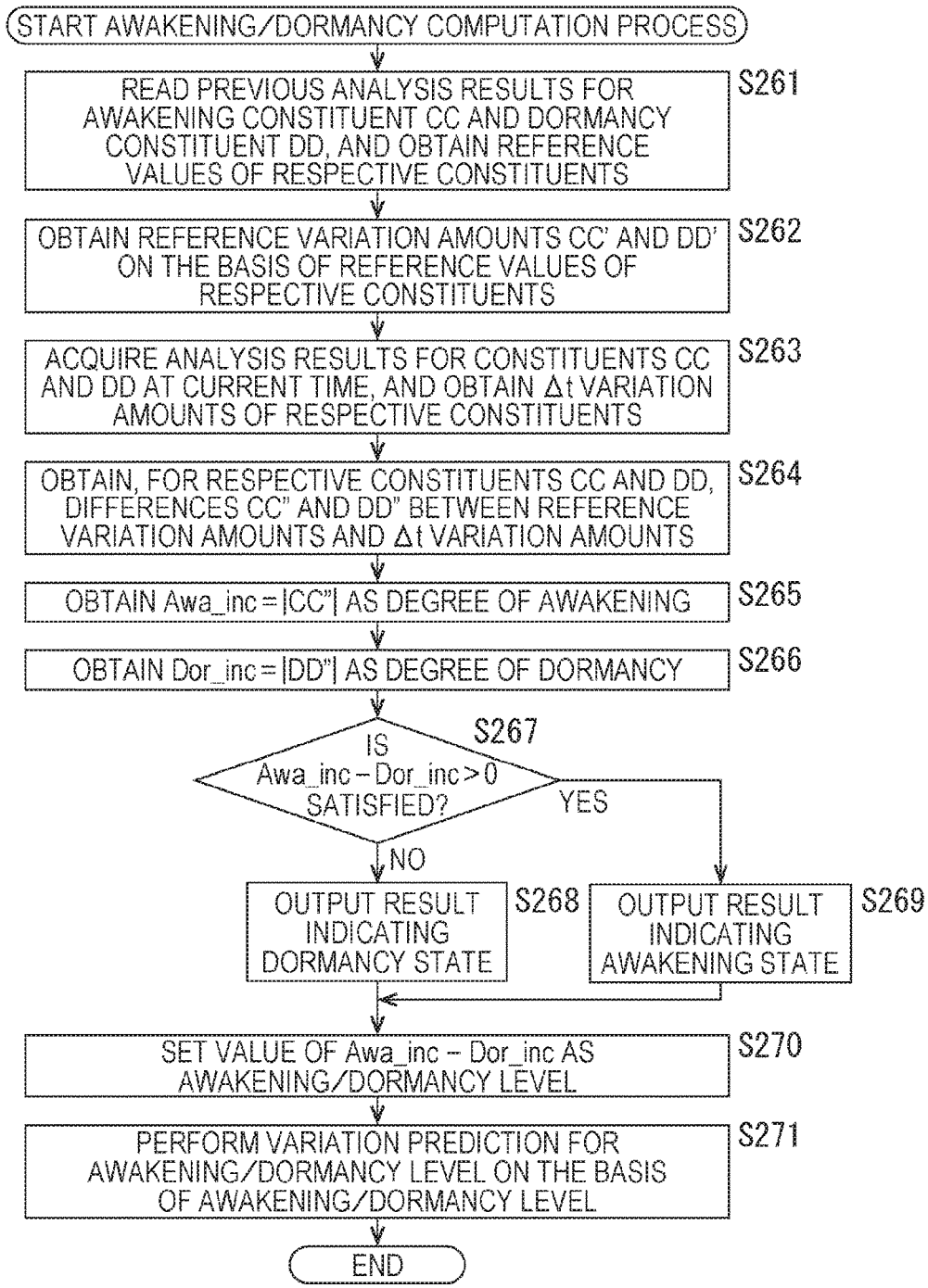
FIG. 17 is a flowchart explaining an awakening/dormancy computation process.

So far, the awakening/dormancy advance prediction computation process has been described. In a manner similar to that for the emotion computation process, a living body state such as awakening and dormancy can be detected using an awakening constituent and a dormancy constituent. Therefore, next, the awakening/dormancy computation process will be described with reference to a flowchart in FIG. 17. Note that the awakening constituent CC is, for example, phenylethanolamine N-methyltransferase (PNMT) or the like, and the dormancy constituent DD is, for example, dopamine β-hydroxylase (DBH) or the like.

In step S261, the living body state detection unit 64 reads previous analysis results for the constituents CC and DD from the recording unit 53, and obtains reference values of the respective constituents. Specifically, since the previously obtained analysis results for the constituents CC and DD are recorded in the recording unit 53, they are read.

In step S262, the living body state detection unit 64 obtains reference variation amounts CC' and DD' on the basis of the reference values of the respective constituents.

In step S263, the living body state detection unit 64 reads analysis results for the constituents CC and DD at a current time from the recording unit 53, and obtains variation amounts CC$\Delta$t and DD$\Delta$t that are $\Delta$t variation amounts of the respective constituents.

In step S264, the living body state detection unit 64 obtains, for the constituents CC and DD, differences CC" and DD" (=$\mu$1 (CC$\Delta$t−CC') and $\mu$2 (DD$\Delta$t−DD')) between the $\Delta$t variation amounts, namely, the variation amounts CC$\Delta$t and DD$\Delta$t, and the reference variation amounts CC' and DD'. Note that $\mu$1 and $\mu$2 are constituent coefficients. In other words, a secretion ratio of each constituent is converted into the coefficient for normalizing a numerical value to be compared.

In step S265, the living body state detection unit 64 calculates a degree Awa_inc of the awakening as |CC"|.

In step S266, the living body state detection unit 64 calculates a degree Dor_inc of the dormancy as |DD"|.

In step S267, the living body state detection unit 64 performs a subtraction to obtain a difference between the degree Awa_inc of the awakening and the degree Dor_inc of the dormancy. The living body state detection unit 64 then determines whether the difference is greater than zero. In other words, the living body state detection unit 64 determines whether the state is the awakening state.

In step S267, when it is determined that the difference between the degree Awa_inc of the awakening and the degree Dor_inc of the dormancy is greater than zero, and the state is the awakening state, the process proceeds to step S269.

In step S269, the living body state detection unit 64 controls the signal antenna 23 to send, to the mobile terminal SP, information indicating that the state is the awakening state, and causes the mobile terminal SP to display the information.

On the other hand, in step S267, when it is determined that the difference between the degree Awa_inc of the awakening and the degree Dor_inc of the dormancy is less than zero, and the state is the dormancy state, the process proceeds to step S268.

In step S268, the living body state detection unit 64 controls the signal antenna 23 to send, to the mobile terminal SP, information indicating that the state is the dormancy state, and causes the mobile terminal SP to display the information.

In step S270, the living body state detection unit 64 sets, as an awakening/dormancy level, the difference between the degree Awa_inc of the awakening and the degree Dor_inc of the dormancy. The living body state detection unit 64 then records the awakening/dormancy level in the recording unit 53.

In step S271, the living body state detection unit 64 performs a variation prediction for the awakening/dormancy level on the basis of the awakening/dormancy level. The living body state detection unit 64 then controls the display element drive unit 28, sends the result of the variation prediction to the mobile terminal SP by controlling the signal antenna 23, and causes the mobile terminal SP to display the result of the variation prediction.

Specifically, for example, when the awakening/dormancy level exceeds a predetermined threshold value, or when the predetermined period of time ΔT elapses from a timing of exceeding the threshold value, the living body state detection unit 64 may cause the mobile terminal SP to display whether the transition to either the awakening or dormancy state might occur. In addition, when the constituent for the awakening increases by A, and the constituent for the dormancy decreases by B, the living body state detection unit 64 may cause the mobile terminal SP to display whether the transition to either the awakening state or the dormancy state might occur after the predetermined period of time ΔT elapses from the timing of exceeding the threshold value.

After the predetermined period of time elapses, the prediction may be able to be performed using data of the variation amounts of the respective constituents to which the state is input by the user, or the prediction may be performed in accordance with a correlation between the variation amounts of the respective constituents. Furthermore, the environmental information such as at the time of wake-up/at the time of eating a meal/commuting/during work/going back home/conversation with a family/before bedtime, is used as the external text mining data, and the prediction may be performed on the basis of a correlation with these items of external text mining data. Furthermore, the prediction after the elapse of the predetermined period of time may be performed by means of the moving average prediction or the approximate value prediction.

<Dry Eyes Determination Process>

Figure 18:
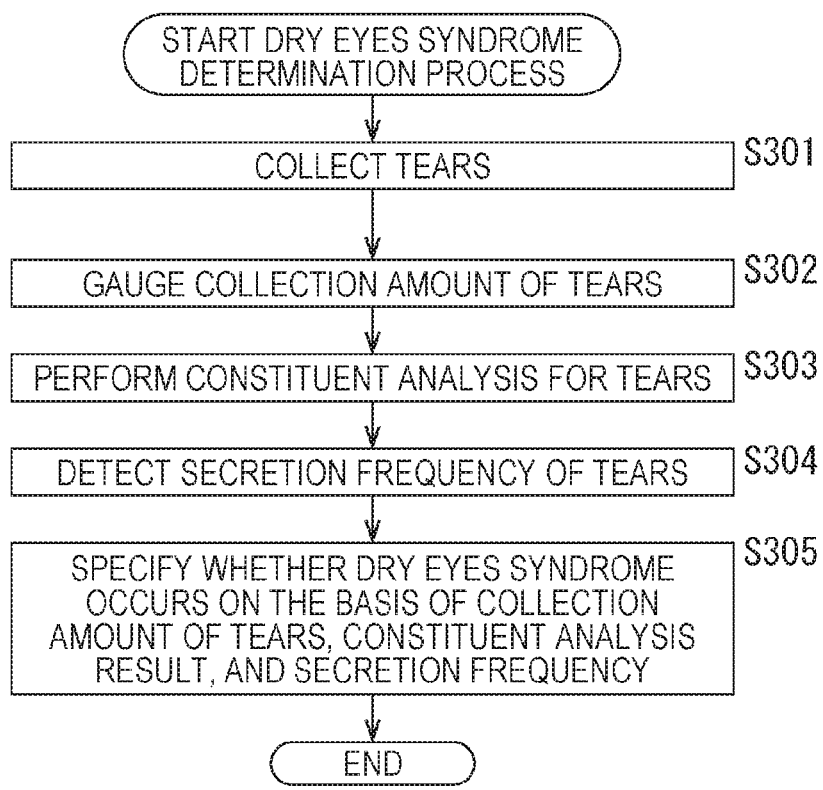
FIG. 18 is a flowchart explaining a dry eyes syndrome determination process.

So far, the example of detecting the information of various living body states from the constituents of the tears has been described. Moreover, information indicating whether dry eyes occur may be detected as the information of the living body state in accordance with the secretion amount, the constituent, and the secretion frequency of the tears. Therefore, next, a dry eyes determination process will be described with reference to a flowchart in FIG. 18.

In step S301, tears on the eyeball are collected by the fine hole 81 through the collection opening G, and supplied to the gauge chamber 82.

In step S302, the gauge chamber 82 gauges the collection amount of the collected tears, and supplies the gauge result to the AD conversion unit 61. The AD conversion unit 61 converts the collection amount of the tears into a digital signal, and supplies the digital signal to the living body state detection unit 64 of the signal processing unit 27.

In step S303, the analysis chamber 86 analyzes the collected tears by means of the spectroscopic analysis, and outputs the analysis result to the AD conversion unit 61. The AD conversion unit 61 digitizes the analysis result, and outputs the digitized analysis result to the living body state detection unit 64 of the signal processing unit 27.

In step S304, the living body state detection unit 64 detects the secretion frequency of the tears, and controls the recording unit 53 to cause the recording unit 53 to record information of the secretion frequency.

In step S305, the biological state detection unit 64 determines whether the dry eyes syndrome occurs on the basis of the collection amount of the tears, the constituent analysis result, and the secretion frequency of the tears. The biological state detection unit 64 then controls the signal antenna 23 to send the determination result to the mobile terminal SP, and cause the mobile terminal SP to display the determination result.

Owing to the above-mentioned processes, the determination result as to whether the dry eyes syndrome occurs can be detected as the living body information of the user, and the user can be notified of the determination result. In addition, data of the collection amount of the tears, the constituent analysis result, and the secretion frequency of the tears may be sent to an external device through the signal antenna 23, and whether the dry eyes syndrome occurs may be estimated by means of the external device itself or a determination system using the external device and a data server.

Furthermore, in accordance with the estimation result, a lacrimal gland may be chemically stimulated in such a manner that lachrymator is secreted by an effector having a container in which the lachrymator is stored in advance, or the lacrimal gland may be physically stimulated by light, electricity, contact with a structure or the like, whereby tears may be forcibly secreted. Moreover, a display for asking the user to perform rehabilitation operation for alleviating or curing the dry eyes syndrome may be provided on a display tool such as a smartphone. Alternatively, such a system may be employed that the data are stored in a server that can be shared with a hospital or the like, and a specialist prescribes advice or medicine for the user.

<First Modification>

So far, the examples of the processes of determining whether the state is the living body state A or B on the basis of, for example, whether the difference between the respective degrees of the constituent that contributes to the living body state A and the constituent that contributes to the living body state B is positive have been described. Alternatively, for example, a threshold value may be set for each constituent, and whether the state is the living body state A or B may be determined on the basis of a relation with each threshold value.

Figure 19:
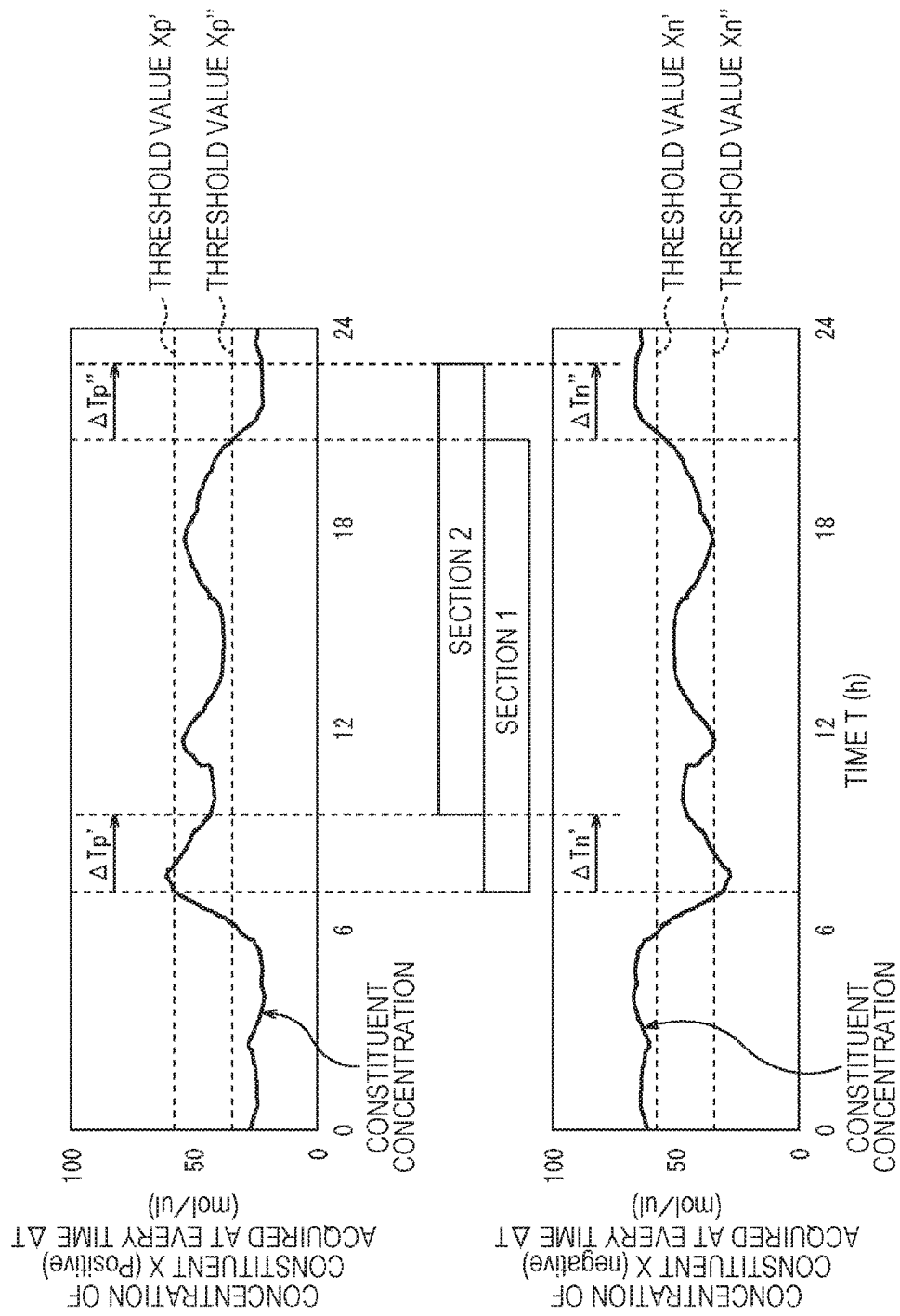
FIG. 19 is a flowchart explaining a cumulated constituent of tears and a prediction of an emotion level.

Specifically, a section from a timing when a concentration of a constituent X (positive) that contributes to the affectivity (positive) becomes greater than a threshold value Xp' as illustrated in the upper row of FIG. 19 and a concentration of a constituent X (negative) that contributes to the affectivity (negative) becomes less than a threshold value Xn" as illustrated in the lower row of FIG. 19 until the concentration of the constituent X (positive) that contributes to the affectivity (positive) becomes less than a threshold value Xp" and the concentration of the constituent X (negative)

that contributes to the affectivity (negative) exceeds a threshold value Xn' may be set to the affective (positive) state indicated by section 1.

The constituent X (positive) is, for example, adrenaline or the like, and the constituent X (negative) from the initial state is, for example, adrenocorticotropic hormone (ACTH), noradrenaline or the like.

In addition, a section from a timing when a predetermined period of time $\Delta Tp'$, $\Delta Tn'$ elapses from the timing when the affective (positive) state is satisfied until a timing when a predetermined period of time $\Delta Tp''$, $\Delta Tn''$ elapses from the timing when the affective (positive) state becomes not satisfied may be set as the affective (positive) state as indicated by section 2.

<Second Modification>

So far, the example of setting whether the state is the affective (positive) state or the affective (negative) state on the basis of the mutual conditions between the constituent X (positive) that contributes to the affectivity (positive) and the constituent X (negative) that contributes to the affectivity (negative) has been described. Alternatively, for example, whether the state is the affective (positive) state or the affective (negative) state may be set in accordance with a condition of either one them.

Figure 20:
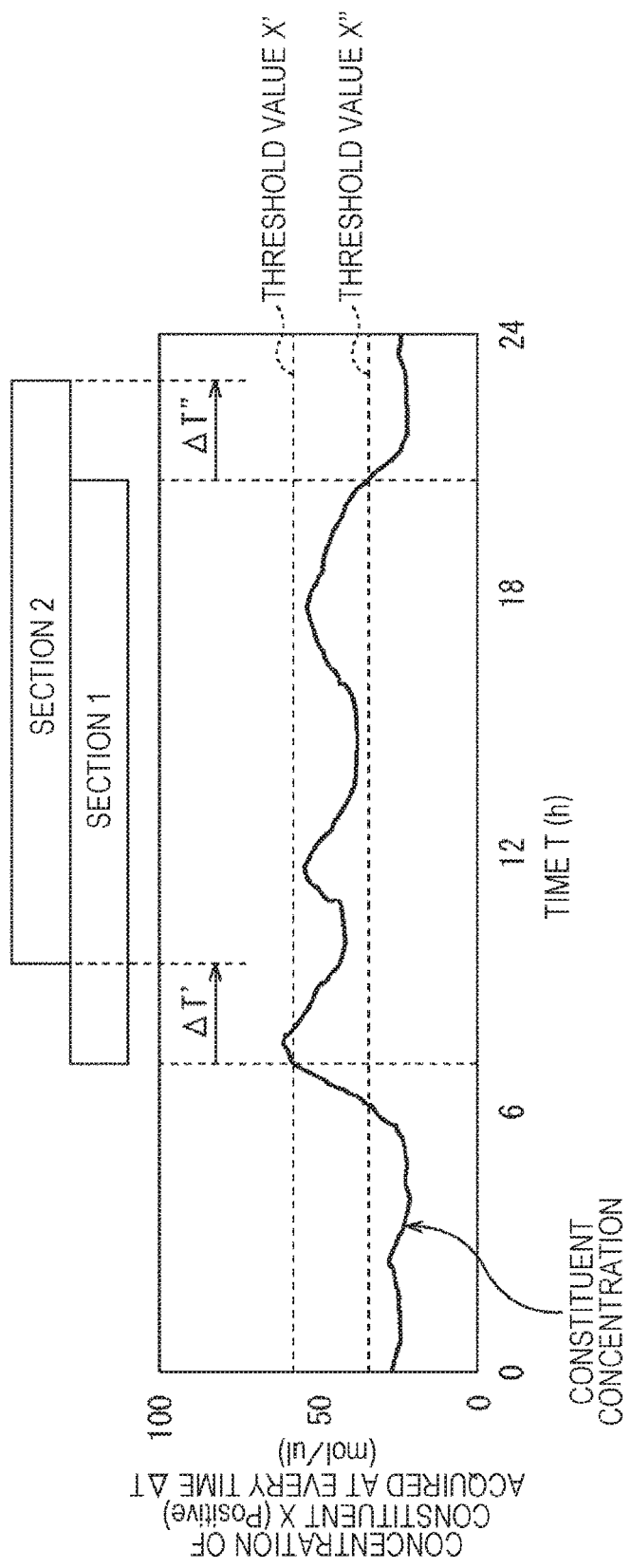
FIG. 20 is a diagram explaining a cumulated constituent of tears and another prediction of an emotion level.

For example as illustrated in FIG. 20, setting may be performed on the assumption that section 1 from when the concentration of the constituent X (positive) that contributes to the affectivity (positive) becomes greater than a threshold value X' until it becomes less than a threshold value X" is the affective (positive) state, and other sections are the affective (negative) state. In this case, the constituent X (positive) that contributes to the affectivity (positive) is, for example, the above-mentioned constituent N or the like, e.g., adrenaline or the like.

Alternatively, as illustrated in FIG. 20, on the assumption that section 2 from a timing when a predetermined period of time $\Delta T'$ elapses from the timing when the concentration of the constituent X (positive) that contributes to the affectivity (positive) becomes greater than the threshold value X' until a timing when a predetermined period of time $\Delta T''$ elapses from the timing when it becomes less than the threshold value X" is the affective (positive) state, and other sections are the affective (negative) state, they may be grasped as an omen of a subsequent transition. In this case, the constituent X (positive) that contributes to the affectivity (positive) is, for example, the above-mentioned constituent S or the like, e.g., phenylethanolamine N-methyltransferase or the like.

Figure 21:
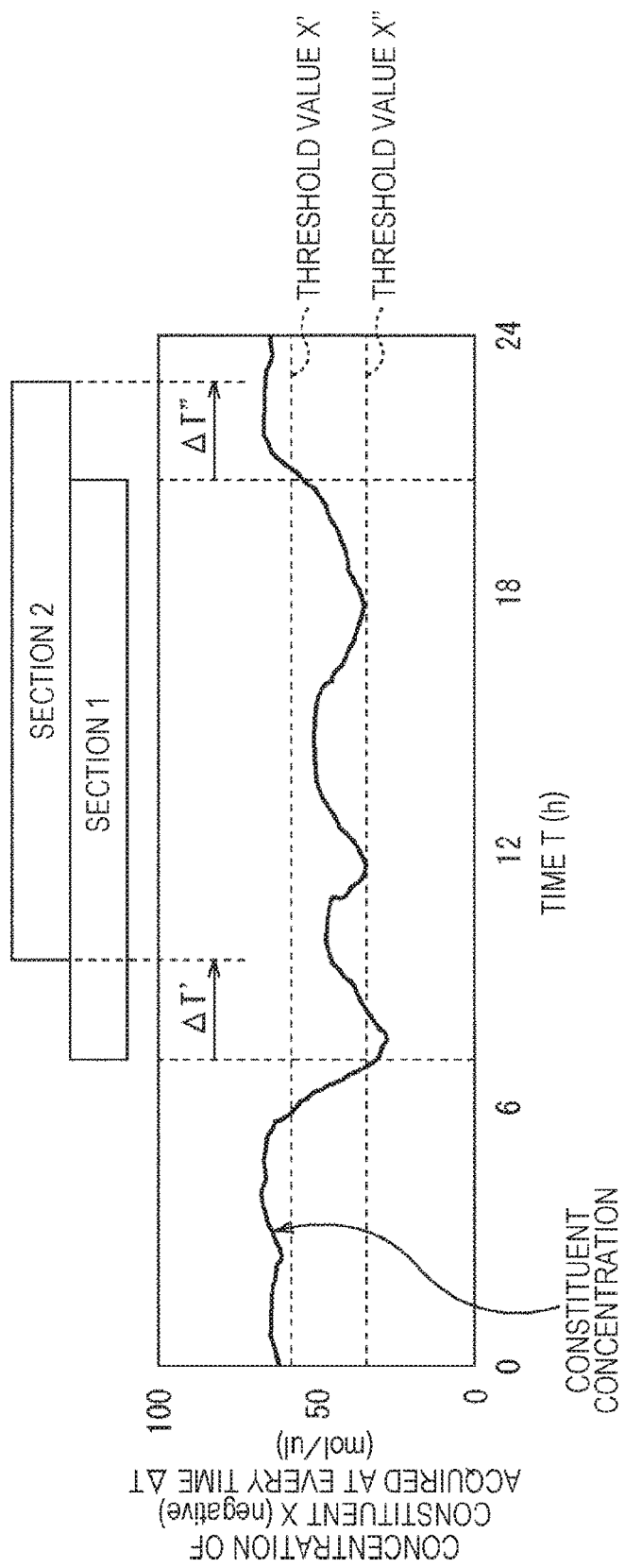
FIG. 21 is a diagram explaining a cumulated constituent of tears and still another prediction of an emotion level.

In a similar manner, for example, as illustrated in FIG. 21, setting may be performed on the assumption that section 1 from when the concentration of the constituent X (negative) that contributes to the affectivity (negative) becomes less than the threshold value X" until it becomes greater than the threshold value X' is the affective (negative) state, and other sections are the affective (positive) state. In this case, the constituent X (negative) that contributes to the affectivity (negative) is, for example, the above-mentioned constituent S or the like, e.g., phenylethanolamine N-methyltransferase or the like.

Alternatively, as illustrated in FIG. 21, on the assumption that a section from a timing when the predetermined period of time $\Delta T'$ elapses from the timing when the concentration of the constituent X (negative) that contributes to the affectivity (negative) becomes less than the threshold value X" until a timing when the predetermined period of time $\Delta T''$ elapses from the timing when it becomes greater than the threshold value X' is the affective (negative) state, and other sections are the affective (positive) state, they may be grasped as an omen of a subsequent transition. In this case, the constituent X (negative) that contributes to the affectivity (negative) is, for example, the above-mentioned constituent N or the like, e.g., adrenaline or the like.

<Third Modification>

The variation prediction for the advance prediction emotion level or the emotion level may be performed in accordance with specific operation of the user.

Figure 22:
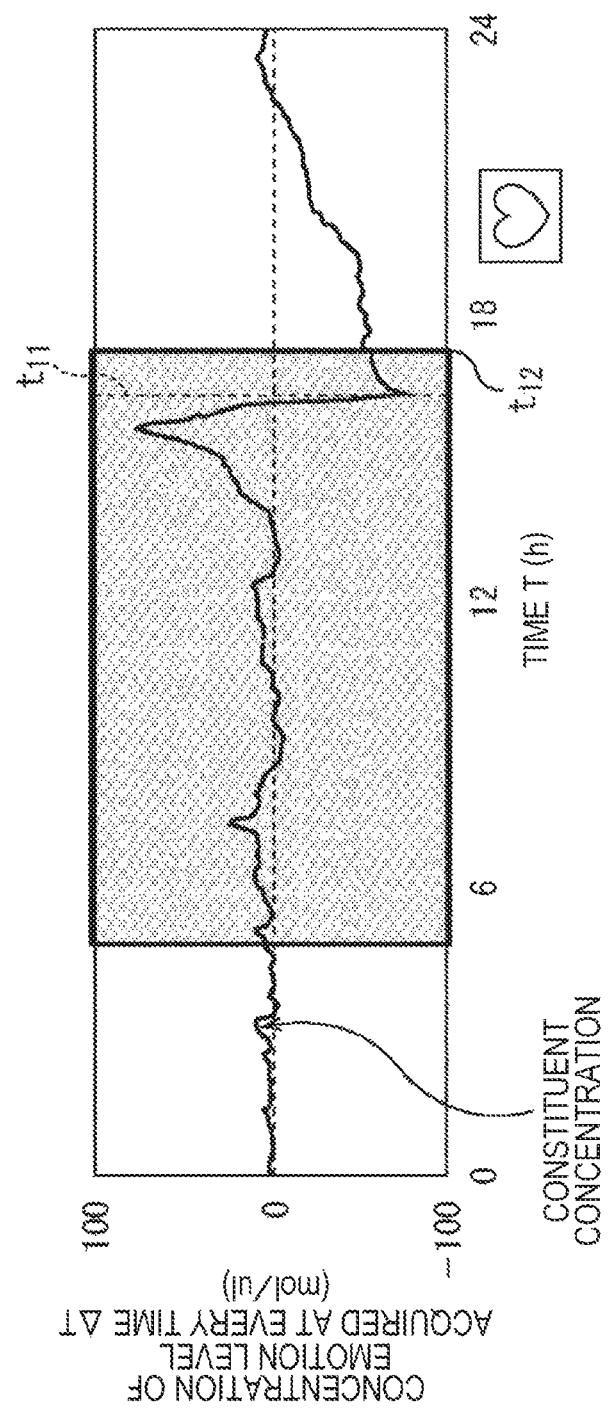
FIG. 22 is a diagram explaining a prediction of an emotion level.

Specifically, as illustrated in FIG. 22, in a case where operation of affixing a stamp (for example, a heart in the drawing) indicating the affective (negative) state is performed at a timing of time t12, ranking of the emotion levels within a range from this timing surrounded by a square frame in the drawing is obtained, and a period of time from the lowest value until the emotion level becomes a state of zero is predicted.

Figure 23:
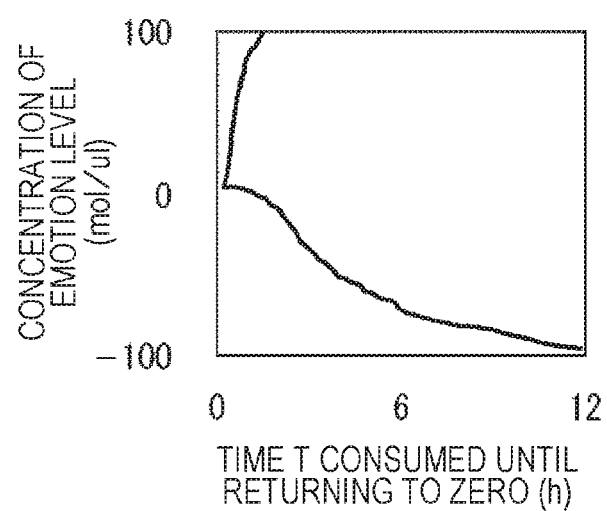
FIG. 23 is a diagram explaining a prediction of an emotion level.

More specifically, as illustrated in FIG. 23, a distribution of average time until the emotion level returns to zero is obtained for each value of the emotion level, whereby the approximate time when the emotion level becomes zero can be predicted.

Therefore, in the case of FIG. 22, since the emotion level is lowest at time t11, this value is applied to the graph in FIG. 23, whereby the period of time to zero can be predicted.

In addition, a waveform pattern of the earlier emotion level may be stored, and the prediction may be performed by means of matching. Note that the advance prediction emotion level can also be predicted using a method similar to that for the emotion level.

<Fourth Modification>

Furthermore, contents to be presented to the user may be determined using a waveform pattern of the above-mentioned advance prediction emotion level or emotion level.

Figure 24:
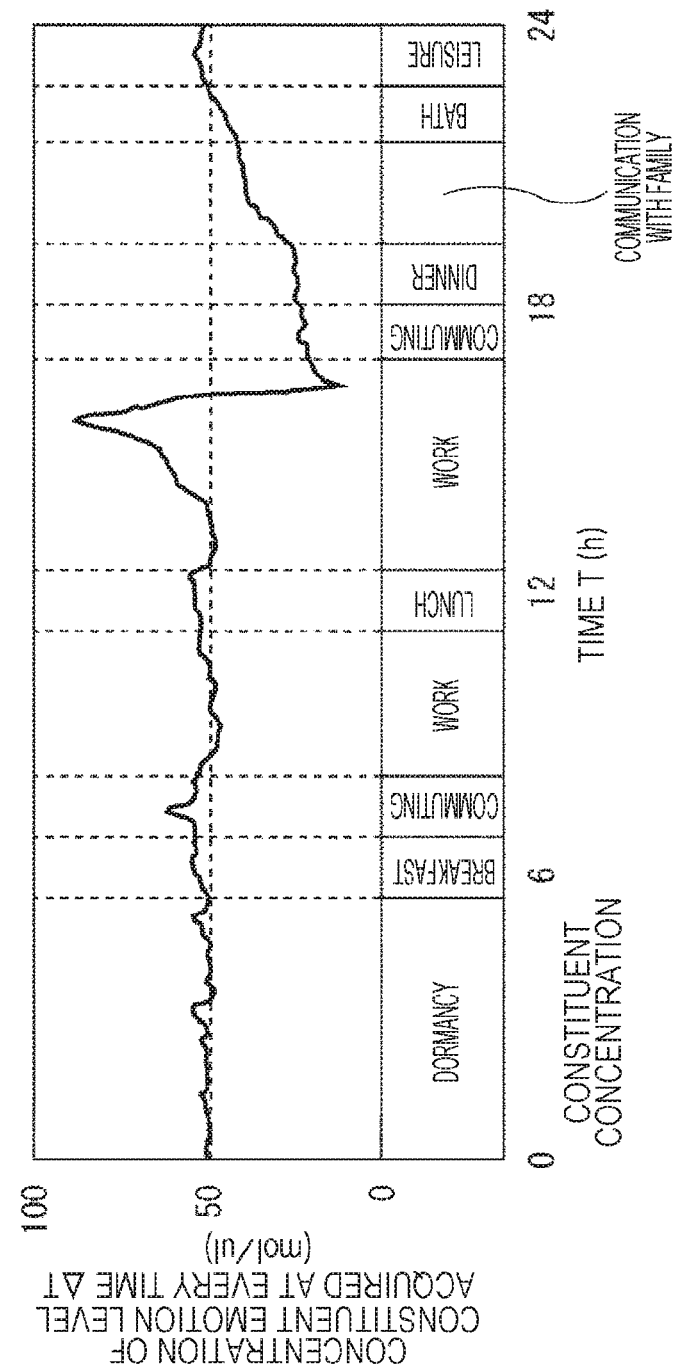
FIG. 24 is a diagram explaining a prediction of an emotion level.

Specifically, as illustrated in FIG. 24, since the waveform pattern of the advance prediction emotion level or the emotion level is associated with a schedule, the schedule is compared, and a criterion for the determination may be presented to a so-called agent. Examples of the criterion for the determination include whether presenting a recommendation now annoys the user, whether there is room for making a joke, or whether presentation of only playing music for refreshment should be given.

For example, at the time of notification of the affectivity (negative), if the notification of the affectivity (negative) is given during work time, it is difficult for the user to refresh herself and cause the state to undergo the transition to the affective (positive) state, and what is worse, work efficiency is liable to be reduced. In this case, therefore, the notification of the affectivity (negative) is suspended. Then, for example, the notification can be given during lunch time or the like when the user can relatively easily cause the state to undergo the transition to the affective (positive) state by going for a walk or the like even though the user receives the notification of the affectivity (negative).

In addition, various types of determination may be performed using the waveform pattern of the advance prediction emotion level or the emotion level in conjunction with, for example, a schedule/history of location information/viewing history/behavior history/search history/operation history.

Second Configuration Example

So far, the configuration of the contact lens type display device including the function of collecting tears and the function of analyzing the collected tears has been described, which corresponds to Case 1 in FIG. 1. Then, next, the contact lens type collection device for tears and the configuration for analyzing the tears collected by the collection device by means of the analysis device AN and causing the mobile terminal or the like to display the analysis result will be described, which corresponds to Case 2 in FIG. 1.

Figure 25:
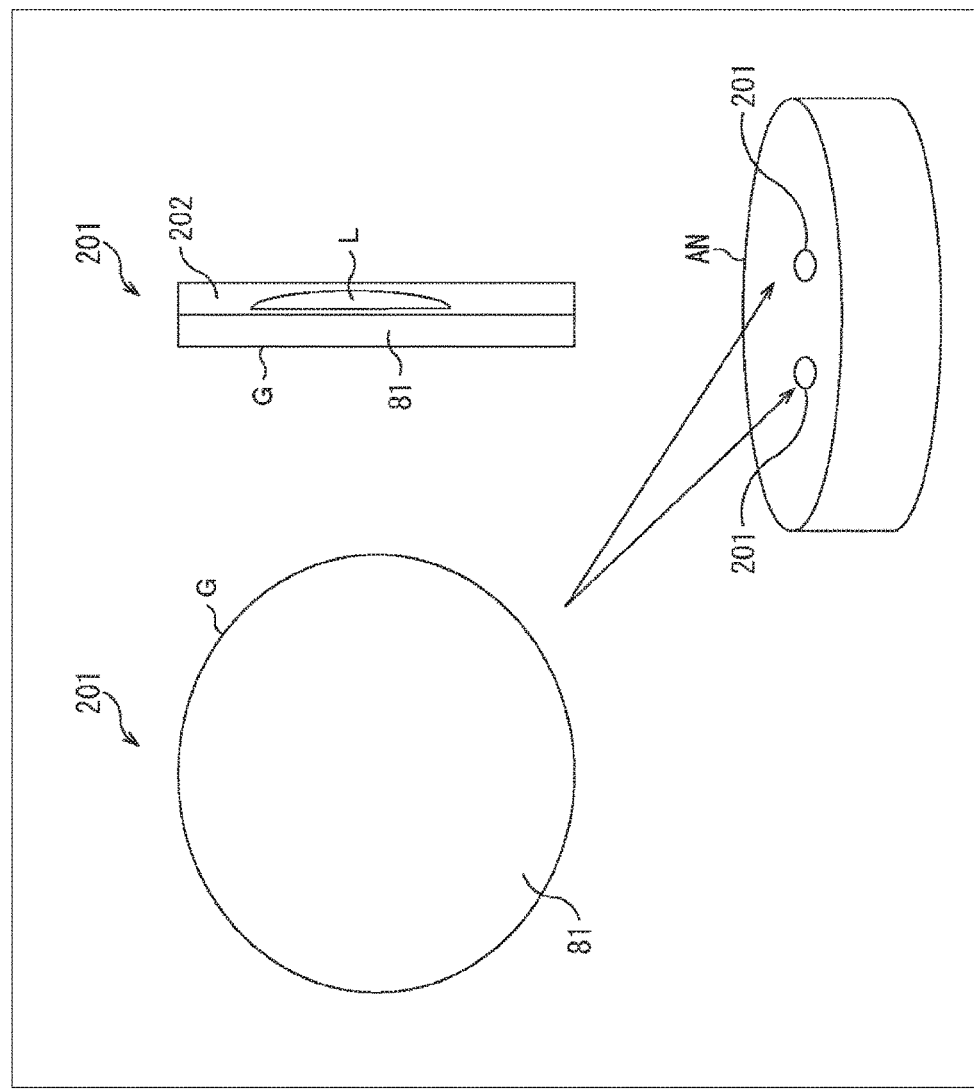
FIG. 25 is a diagram explaining an appearance configuration of a contact lens type collection device for tears and an analysis device to which the present technology is applied.

FIG. 25 is a diagram illustrating the contact lens type collection device for tears and a configuration example for analyzing the tears collected by the collection device by means of the analysis device AN and causing the mobile terminal or the like to display the analysis result. The collection device 201 for tears is illustrated in the upper part of FIG. 25, and the configuration of the analysis device AN is illustrated in the lower part of FIG. 25.

Note that the collection device 201 is a component corresponding to the tear detection unit 26 of the contact lens type display device 11, and provided at the collection opening G in FIG. 2.

More specifically, in a manner similar to that for the collection opening G in FIG. 5, the collection device 201 is provided with the fine hole 81 at a part that comes into contact with the eyeball, and tears are collected using the capillary action, and stored in a storage container 202.

Then, the collection device 201 with the tears collected is stored in the analysis device AN as it is.

<Configuration Example of Analysis Device>

Figure 26:
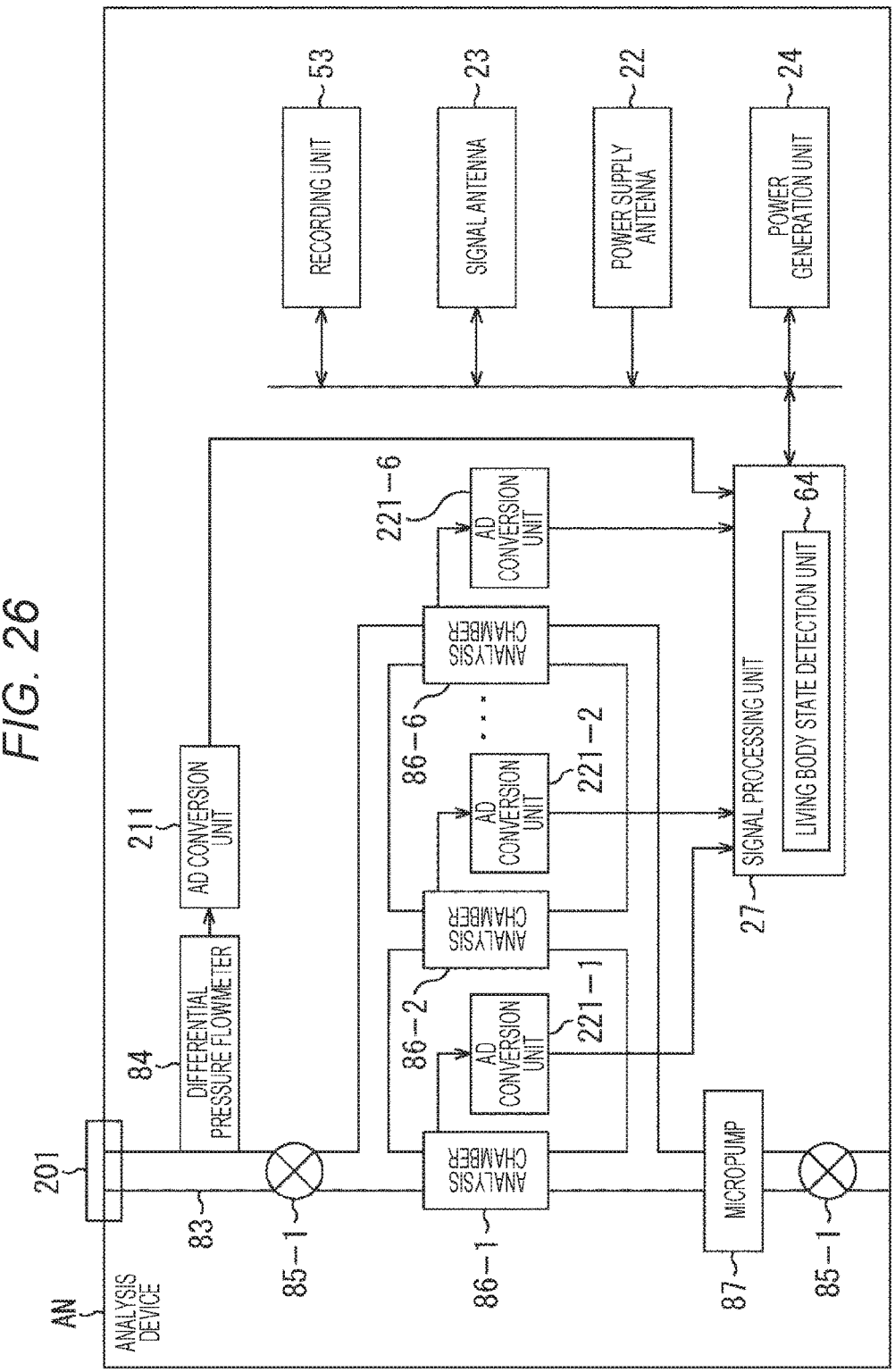
FIG. 26 is a block diagram explaining a configuration for realizing a function of the analysis device.

Next, a configuration example of the analysis device AN in FIG. 26 will be described. Note that, in the analysis device AN in FIG. 26, a component including a function that is the same as the function constituting the display device 11 in FIG. 4 and the tear detection unit 26 in FIG. 5 is denoted by the same reference sign and name, and the description thereof is appropriately omitted. However, although the same function is included, the size is different from that of the component of the display device 11 in FIG. 4 provided within the contact lens type structure.

In other words, the analysis device AN has both the analysis function of the tear detection unit 26 and the living body state detection function of the display device 11. Specifically, the analysis device AN includes the channel 83, the differential pressure flowmeter 84, the control valves 85-1 and 85-2, the analysis chambers 86-1 to 86-5, AD conversion units 211 and 221-1 to 221-5, the micropump 87, the signal processing unit 27, the living body state detection unit 64, the recording unit 53, the signal antenna 23, the power supply antenna 22, and the power generation unit 24.

Note that the analysis device AN is provided with a part on which the collection device 201 can be installed, and provided with the channel 83 from which the tears collected by the storage container 202 of the installed collection device 201 are taken out, and the tears collected therefrom are delivered to the analysis chambers 86-1 to 86-5. The analysis chambers 86-1 to 86-5 detect various constituents, and output the detection results respectively to the AD conversion units 221-1 to 221-5, where the detection results are converted into digital signals and output to the signal processing unit 27. At this time, the differential pressure flowmeter 84 also measures the flow rate of the tears read from the collection device 201, converts the flow rate into a digital signal, and output the digital signal to the signal processing unit 27.

The living body state detection unit 64 of the signal processing unit 27 executes processes similar to the above-mentioned processes on the basis of the analysis results supplied from the analysis chambers 86-1 to 86-5. The living body state detection unit 64 then controls the signal antenna 23 to send information that depends on the analysis result to the mobile terminal SP represented by a smartphone.

Note that since the various processes are similar to those in Case 1, the description thereof is omitted.

Meanwhile, the above-mentioned sequence of processes can be executed by hardware, and can also be executed by software. In a case where the sequence of processes is executed by the software, a program constituting the software is installed from a recording medium on a computer incorporated in dedicated hardware or, for example, on a general-purpose personal computer capable of executing various functions by installing various programs.

Figure 27:
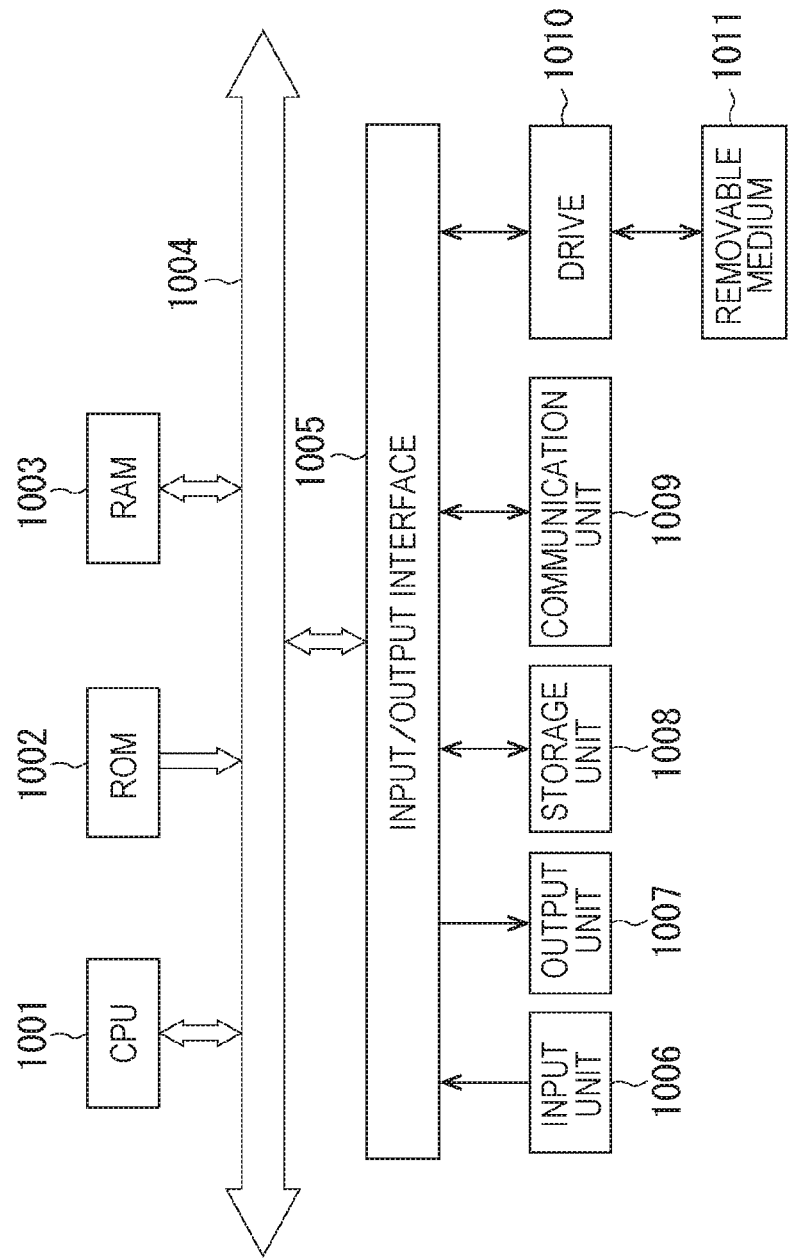
FIG. 27 is a diagram explaining a configuration example of a general-purpose personal computer.

FIG. 27 is a diagram illustrating a configuration example of the general-purpose personal computer. A central processing unit (CPU) 1001 is embedded in the personal computer. An input/output interface 1005 is coupled to the CPU 1001 via a bus 1004. A read only memory (ROM) 1002 and a random access memory (RAM) 1003 are connected to the bus 1004.

An input unit 1006, an output unit 1007, a storage unit 1008, and a communication unit 1009 are connected to the input/output interface 1005. The input unit 1006 includes an input device such as a keyboard and a mouse through which the user inputs an operation command. The output unit 1007 outputs a processing operation screen or an image of the processing result to a display device. The storage unit 1008 includes a hard disk drive or the like in which a program or various types of data are stored. The communication unit 1009 includes a local area network (LAN) adapter or the like, and executes a communication process via a network represented by the Internet. In addition, a drive 1010 is connected. The drive 1010 reads and writes data from and to a removable medium 1011 such as a magnetic disk (including a flexible disk), an optical disk (including a compact disc-read only memory (CD-ROM) and a digital versatile disc (DVD)), a magneto-optical disk (including a mini disc (MD)), or a semiconductor memory.

The CPU 1001 executes the various processes in accordance with a program stored in the ROM 1002 or a program read from the removable medium 1011 such as a magnetic disk, an optical disk, a magneto-optical disk, or a semiconductor memory, installed on the storage unit 1008, and loaded from the storage unit 1008 on the RAM 1003. Data or the like required for the CPU 1001 to execute the various processes are appropriately stored in the RAM 1003.

In the computer configured as mentioned above, the CPU 1001 loads, for example, the program stored in the storage unit 1008 on the RAM 1003 via the input/output interface 1005 and the bus 1004, and executes the program, whereby the above-mentioned sequence of processes is performed.

The program that is executed by the computer (CPU 1001) can be recorded in the removable medium 1011 serving as, for example, a package medium or the like, and provided. Alternatively, the program can be provided through a wired or wireless transmission medium such as a local area network, the Internet, and digital satellite broadcasting.

In the computer, the program can be installed on the storage unit 1008 via the input/output interface 1005 when the removable medium 1011 is mounted in the drive 1010. Alternatively, the program can be received at the communication unit 1009 via a wired or wireless transmission medium, and installed on the storage unit 1008. Additionally, the program can be installed in advance on the ROM 1002 or the storage unit 1008.

Note that the program that is executed by the computer may be such a program that the processes are performed in time series in the order described in the present description, or may be such a program that the processes are performed parallelly or at a necessary timing, i.e., for example, when a call is performed.

In addition, in the present description, the system means a collection of a plurality of components (devices, modules (parts) or the like), whether all the components exist in the same housing or not. Therefore, both a plurality of devices housed in separate housings and coupled via a network and a single device including a single housing in which a plurality of modules is housed are the systems.

Note that the embodiment of the present technology is not limited to the above-mentioned embodiment, and can be variously changed in a range not departing from the gist of the present technology.

For example, the present technology can take a configuration of cloud computing in which a single function is shared and processed by a plurality of devices in cooperation with each other via a network.

In addition, the respective steps described in the above-mentioned flowcharts can be executed by a single device, or can be shared and executed by a plurality of devices.

Furthermore, in a case where a plurality of processes is included in a single step, the plurality of processes included in the single step can be executed by a single device, or can be shared and executed by a plurality of devices.

Note that the present technology can also take the following configuration.

(1) A detection device including:
an analysis unit configured to perform a constituent analysis for tears gathered from a living body; and
a detection unit configured to detect a state of the living body on the basis of a result of the constituent analysis for the tears.

(2) The detection device according to (1), wherein
the detection unit detects the state of the living body that is determined in accordance with a kind of the tears on the basis of the result of the constituent analysis for the tears.

(3) The detection device according to (1) or (2), wherein
an affective state caused by an emotion of the living body is included in the state of the living body.

(4) The detection device according to (3), wherein
the detection unit specifies whether the state of the living body undergoes a transition to a predetermined affective state on the basis of an analysis result, obtained as the result of the constituent analysis for the tears, for a substance that is secreted when the state of the living body is about to undergo the transition to the predetermined affective state.

(5) The detection device according to (4), wherein
the detection unit specifies whether the state of the living body undergoes a transition to either a first affective state or a second affective state on the basis of a degree of likelihood of the transition to the first affective state calculated on the basis of an analysis result, obtained as the result of the constituent analysis for the tears, for a substance that is secreted when the state of the living body is about to undergo the transition to the first affective state, and a degree of likelihood of the transition to the second affective state calculated on the basis of an analysis result, obtained as the result of the constituent analysis for the tears, for a substance that is secreted when the state of the living body is about to undergo the transition to the second affective state.

(6) The detection device according to (5), wherein
the detection unit further calculates an advance prediction emotion level indicating a degree of a state of the living body to which the state of the living body is estimated to be going to undergo a transition on the basis of the degree of the likelihood of the transition to the first affective state and the degree of the likelihood of the transition to the second affective state.

(7) The detection device according to (6), wherein
the detection unit predicts a variation in the advance prediction emotion level at a time after a current time on the basis of the advance prediction emotion level.

(8) The detection device according to (3), wherein
the detection unit specifies the state of the living body on the basis of an analysis result, obtained as the result of the constituent analysis for the tears, for a substance that is secreted a lot when the state of the living body is a predetermined affective state.

(9) The detection device according to (8), wherein
the detection unit specifies whether the state of the tears is either a first affective state or a second affective state on the basis of a degree of likelihood of the first affective state calculated on the basis of an analysis result, obtained as the result of the constituent analysis for the tears, for a substance that is secreted a lot during the first affective state, and a degree of likelihood of the second affective state calculated on the basis of an analysis result, obtained as the result of the constituent analysis for the tears, for a substance that is secreted a lot during the second affective state.

(10) The detection device according to (9), wherein
the detection unit further calculates an emotion level indicating a degree of the affective state of the living body on the basis of the degree of the likelihood of the first affective state and the degree of the likelihood of the second affective state.

(11) The detection device according to (10), wherein
the detection unit predicts a variation in the emotion level at a time after a current time on the basis of the emotion level.

(12) The detection device according to (2), wherein
a state caused by a stimulus to the living body is included in the state of the living body.

(13) The detection device according to (12), wherein
the detection unit specifies whether the state of the living body is the state caused by the stimulus to the living body or an affective state caused by an emotion of the living body to which the state of the living body undergoes a transition when the living body keeps feeling an aching pain on the basis of an analysis result, obtained as the result of the constituent analysis for the tears, for a substance that is secreted when there is the stimulus to the living body or when the living body feels the aching pain.

(14) The detection device according to (13), wherein
the detection unit specifies whether the state of the living body is the state caused by the stimulus to the living body or the affective state caused by the emotion of the living body on the basis of a length of a period of time which is based on the analysis result for the substance that is secreted when there is the stimulus to the living body or when the living body feels the aching pain, and during which a value indicating a secretion amount of the substance is equal to or greater than a predetermined threshold value.

(15) The detection device according to (13) or (14), wherein
the detection unit calculates a stimulus level or an aching pain level for the living body on the basis of the analysis result for the substance that is secreted when there is the stimulus to the living body or when the living body feels the aching pain.

(16) The detection device according to (15), wherein
the detection unit predicts a variation in the stimulus level or the aching pain level at a time after a current time on the basis of the stimulus level or the aching pain level.

(17) The detection device according to any of (1) to (16), wherein
the detection unit specifies a secretion level of the tears of the living body on the basis of an analysis result, obtained as the result of the constituent analysis for the tears, for a specific substance.

(18) The detection device according to any of (1) to (17), wherein
the detection device is attachable and detachable to and from an eyeball.

(19) A detection method including the steps of:
performing a constituent analysis for tears gathered from a living body; and
detecting a state of the living body on the basis of a result of the constituent analysis for the tears.

(20) A program that causes a computer to execute a process including:
an analysis step of performing a constituent analysis for tears gathered from a living body; and
a detection step of detecting a state of the living body on the basis of a result of the constituent analysis for the tears.

REFERENCE SIGNS LIST

11 Display device
21 Display region
25 Posture detection unit
26-1 to 26-3, 26 Tear detection unit
27 Signal processing unit
61 AD conversion unit
64 Living body state detection unit
86, 86-1 to 86-5 Analysis chamber
101 Excitation light source
102 Analysis space
103 Heater
104 Lens
105 Air gap
106 Light receiver

The invention claimed is:

1. A detection device, comprising:
at least one processor configured to:
perform a constituent analysis for tears gathered from a living body;
determine a state of the living body based on a result of the constituent analysis for the tears; and
determine a transition of the state of the living body is to one of a first affective state or a second affective state, wherein the determination of the transition is based on:
a degree of likelihood of the transition to the first affective state, wherein:
the degree of likelihood of the transition to the first affective state is calculated based on a first analysis result for a first substance secreted when the state of the living body is about to undergo the transition to the first affective state,
the first analysis result is obtained as the result of the constituent analysis for the tears, and
the first analysis result is based on a first length of a first period of time for the first substance is secreted and a first value that indicates a secretion amount of the first substance is one of equal to or greater than a first threshold value; and
a degree of likelihood of the transition to the second affective state, wherein:
the degree of likelihood of the transition to the second affective state is calculated based on a second analysis result for a second substance secreted when the state of the living body is about to undergo the transition to the second affective state,
the second analysis result is obtained as the result of the constituent analysis for the tears, and
the second analysis result is based on a second length of a second period of time for the second substance is secreted and a second value that indicates a secretion amount of the second substance is one of equal to or greater than a second threshold value.

2. The detection device according to claim 1, wherein
the at least one processor is further configured to determine the state of the living body in accordance with a kind of the tears based on the result of the constituent analysis for the tears.

3. The detection device according to claim 2, wherein
a specific state based on a stimulus to the living body is included in the state of the living body.

4. The detection device according to claim 3, wherein:
the at least one processor is further configured to determine that the state of the living body is one of the state based on the stimulus to the living body or an affective state,
the affective state is based on an emotion of the living body to which the state of the living body undergoes the transition when the living body feels an aching pain, and
the determination that the state of the living body is one of the state based on the stimulus to the living body or the affective state is based on:
a third analysis result, wherein
the third analysis result is obtained as the result of the constituent analysis for the tears for a third substance secreted when there is one of the stimulus to the living body or when the living body feels the aching pain.

5. The detection device according to claim 4, wherein:
the at least one processor is further configured to determine that the state of the living body is one of the state based on the stimulus to the living body or the affective state,
the affective state is based on the emotion of the living body,
the determination that the state of the living body is one of the state based on the stimulus to the living body or the affective state is based on:
a third length of a third period of time, wherein
the third length of the third period of time is based on the third analysis result for the third substance secreted when there is one of the stimulus to the living body or when the living body feels the aching pain, and
a third value indicating a secretion amount of the third substance is one of equal to or greater than a third threshold value.

6. The detection device according to claim 4, wherein
the at least one processor is further configured to calculate one of a stimulus level or an aching pain level for the living body based on the third analysis result for the third substance secreted when there is one of the stimulus to the living body or when the living body feels the aching pain.

7. The detection device according to claim 6, wherein the at least one processor is further configured to predict a variation in one of the stimulus level or the aching pain level at a time after a current time based on one of the stimulus level or the aching pain level at the current time.

8. The detection device according to claim 1, wherein an affective state based on an emotion of the living body is included in the state of the living body.

9. The detection device according to claim 1, wherein the at least one processor is further configured to calculate an advance prediction emotion level indicating a degree of an upcoming state of the living body to which the state of the living body is estimated to be going to undergo the transition based on the degree of the likelihood of the transition to the first affective state and the degree of the likelihood of the transition to the second affective state.

10. The detection device according to claim 9, wherein the at least one processor is further configured to predict a variation in the advance prediction emotion level at a time after a current time based on the advance prediction emotion level at the current time.

11. The detection device according to claim 1, wherein the at least one processor is further configured to calculate an emotion level indicating a degree of an affective state of the living body based on the degree of the likelihood of the transition to the first affective state and the degree of the likelihood of the transition to the second affective state.

12. The detection device according to claim 11, wherein the at least one processor is further configured to predict a variation in the emotion level at a time after a current time based on the emotion level at the current time.

13. The detection device according to claim 1, wherein the at least one processor is further configured to determine a secretion level of the tears of the living body based on a fourth analysis result for a specific substance, and the fourth analysis result is obtained as the result of the constituent analysis for the tears.

14. The detection device according to claim 1, wherein the detection device is one of attachable to or detachable from an eyeball.

15. A detection method, comprising:
performing a constituent analysis for tears gathered from a living body;
determining a state of the living body based on a result of the constituent analysis for the tears, and
determining a transition of the state of the living body is to one of a first affective state or a second affective state, wherein the determination of the transition is based on:
  a degree of likelihood of the transition to the first affective state, wherein:
    the degree of likelihood of the transition to the first affective state is calculated based on a first analysis result for a first substance secreted when the state of the living body is about to undergo the transition to the first affective state,
    the first analysis result is obtained as the result of the constituent analysis for the tears, and
    the first analysis result is based on a first length of a first period of time for the first substance is secreted and a first value that indicates a secretion amount of the first substance is one of equal to or greater than a first threshold value; and
  a degree of likelihood of the transition to the second affective state, wherein:
    the degree of likelihood of the transition to the second affective state is calculated based on a second analysis result for a second substance secreted when the state of the living body is about to undergo the transition to the second affective state,
    the second analysis result is obtained as the result of the constituent analysis for the tears, and
    the second analysis result is based on a second length of a second period of time for the second substance is secreted and a second value that indicates a secretion amount of the second substance is one of equal to or greater than a second threshold value.

16. A non-transitory computer-readable medium having stored thereon computer-executable instructions that, when executed by at least one processor, cause a computer to execute operations, the operations comprising:
performing a constituent analysis for tears gathered from a living body;
determining a state of the living body based on a result of the constituent analysis for the tears, and
determining a transition of the state of the living body is to one of a first affective state or a second affective state, wherein the determination of the transition is based on:
  a degree of likelihood of the transition to the first affective state, wherein:
    the degree of likelihood of the transition to the first affective state is calculated based on a first analysis result for a first substance secreted when the state of the living body is about to undergo the transition to the first affective state,
    the first analysis result is obtained as the result of the constituent analysis for the tears, and
    the first analysis result is based on a first length of a first period of time for the first substance is secreted and a first value that indicates a secretion amount of the first substance is one of equal to or greater than a first threshold value; and
  a degree of likelihood of the transition to the second affective state, wherein:
    the degree of likelihood of the transition to the second affective state is calculated based on a second analysis result for a second substance secreted when the state of the living body is about to undergo the transition to the second affective state,
    the second analysis result is obtained as the result of the constituent analysis for the tears, and
    the second analysis result is based on a second length of a second period of time for the second substance is secreted and a second value that indicates a secretion amount of the second substance is one of equal to or greater than a second threshold value.

17. A detection device, comprising:
at least one processor configured to:
  perform a constituent analysis for tears gathered from a living body;

determine a state of the living body based on a result of the constituent analysis for the tears; and determine whether a state of the tears is one of a first affective state or a second affective state based on:
- a degree of likelihood of the first affective state calculated based on a first analysis result for a first substance secreted during the first affective state, wherein the first analysis result is obtained as the result of the constituent analysis for the tears, and
- a degree of likelihood of the second affective state calculated based on a second analysis result for a second substance secreted during the second affective state, wherein the second analysis result is obtained as the result of the constituent analysis for the tears.

* * * * *